United States Patent [19]
Barg et al.

[11] Patent Number: 6,114,602
[45] Date of Patent: Sep. 5, 2000

[54] METHOD FOR THE INDUCTION OF GENETIC PARTHENOCARPY IN PLANTS

[75] Inventors: Rivka Barg; Yehiam Salts Salts, both of Rehovot, Israel

[73] Assignee: State of Israel/Ministry of Agriculture, Bet Dagan, Israel

[21] Appl. No.: 09/125,287

[22] PCT Filed: Feb. 13, 1997

[86] PCT No.: PCT/IL97/00051

§ 371 Date: Nov. 9, 1998

§ 102(e) Date: Nov. 9, 1998

[87] PCT Pub. No.: WO97/30165

PCT Pub. Date: Aug. 21, 1997

[30] Foreign Application Priority Data

Feb. 14, 1996 [IL] Israel ......................................... 117139

[51] Int. Cl.[7] ........................... C12N 15/82; C12N 15/84; A01H 5/00; A01H 5/08
[52] U.S. Cl. .................. 800/290; 435/69.1; 435/430; 435/469; 536/24.1; 800/287; 800/288; 800/294; 800/298; 800/317.4
[58] Field of Search ................. 435/69.1, 320.1, 435/410, 411, 419, 468, 469, 430; 536/23.6, 24.1; 800/278, 287, 288, 290, 294, 295, 298, 317.4

[56] References Cited

U.S. PATENT DOCUMENTS 5,175,095  12/1992  Marineau et al. ...................... 435/69.1

OTHER PUBLICATIONS

O. Nilsson and O. Olsson, Getting to the root: The role of the *Agrobacterium rhizogenes* rol genes in the formation of hairy roots, *Physiologia Plantarum 100*: 1997, pp. 463–473.

A. Delbarre, et al., The rolB Gene of *Agrobacterium rhizogenes* Does Not Increase the Auxin Sensitivity of Tabacco Protaplasts by Modifying the Intracellular Auxin Concentration, *Plant Physiol,* vol. 105, 1994, pp. 563–569.

Maurel et al., *Plant Physiol.* 1991, vol. 97, pp. 212–216.

van Altvorst et al, Plant Sci., vol. 83, pp. 77–85, 1992.

Egea–Cortines et al, Physiol. Plant., vol. 87, pp. 14–20, 1993.

Horsch et al, Science, vol. 227, pp. 1229–1231, 1985.

*Primary Examiner*—Lynette R. F. Smith
*Assistant Examiner*—Ashwin D. Mehta
*Attorney, Agent, or Firm*—Lowe Hauptman Gopstein Gilman & Berner

[57] ABSTRACT

The present invention provides an improved method for the production of genetic parthenocarpy in plants, which includes the steps of: providing a cassette including a DNA coding for modulation of auxin effects in plants, such as the rolB gene, and a promoter specific for the ovary between anthesis and early fruit development to control the DNA sequence and introducing the cassette into a plant. Preferably, the DNA is introduced by transformation of plant material (including seed derived cotyledons), and regeneration of transformed plants. Preferably the method also includes the step of screening the plant for either facultative or obligatory parthenocarpic characteristics.

9 Claims, 21 Drawing Sheets

|      |            |            |            |            |            |            |            |
|------|------------|------------|------------|------------|------------|------------|------------|
| 1    | ATGCATCCCA | AATAGGCGAG | TGAGATGGAA | GGGAGGCAAT | GACACGAAAT | TTGTCTATGT | GTCCTAGATA | TGTAAGAATT |
| 81   | CACTGATATA | TTGAGTGTAT | CTAGAATAAA | TTAACTTGAT | TTTGAGTCCA | TGTATTAGA  | GATACATGTA | TCTGGACATA |
| 161  | TCAAAGTCTG | ATAAAATTCA | TAATATTAAA | ACATAGAGTG | TCTTTAAGTA | ATTAGCTCAT | ACACTAGAAT | GATTTTTGTA |
| 241  | AGTTACACTT | AAATAAATTG | TTTTGGCCCA | TGAGCCAACT | GACCCCAATC | AAGCCTCAAG | GGCTTATATG | AATCGAGTTT |
| 321  | ATAAGCCCTA | GTTTCAAATG | AGCTTGAAAA | ATTCTATCTC | AACTATATCC | AAATAATAGA | TTGGATTGGA | TCGAaTCCCA |
| 401  | TGGGCTACGC | ATTTTGATAG | CTCTAGTTGT | AACCCTAACT | AATGATGAAA | ATATTTTTGA | CATGATATTT | ATTTTATTAC |
| 481  | CACAATTATT | TTAATATTTA | TTTTATACAT | AATATATTTC | TTATAAAATT | ACTACACATA | ATTGTCTGAT | GACTGTAGAA |
| 561  | GAGTAGTTGA | CAAAATATTA | TCGCAATGTC | ATTGTTATTA | TAGGTACAAA | TTATTAAGTG | AAAGTAGAAT | ATAACGTGAA |
| 641  | ATCGAATTAA | AAAAATAATC | AGATTGTAAT | GAAATATTAT | TAGAGAGAAG | TATTAAAGTA | CCTATAAACT | TGGCACAAAT |
| 721  | TATTAGTTTT | ATTTCTGTAC | TATTGACAAC | CTTAAAAAACT | ACTTGACTAA | CTAAACTTAG | ATACACCTAA | TTTTTTGTAG |
| 801  | GAGCATGAAA | CTCTTAATGA | ATGGCCAAGA | GAAGTGTTGA | AAGCACCCCC | AAACTTGATG | AGAATTAGA  | GTGTATTTCA |
| 881  | CCCATATTGC | AAGATTGTAA | GTGTATTTAA | ATTTAGTTAA | TCAATTAAAT | AAATGTATTT | TGAATTCCAA | TAATTCAAGG |
| 961  | ATGAAACAAA | TAGTTCATAT | TGAATTTAAA | TGTTTTTTGA | ATACTTCTTT | TTTCTCCAAT | ATTGACTAAC | TAGTACAACC |
| 1041 | AGGTTTGATT | ATGATTAGA  | TTTGTACCAC | ATAAGATTAT | TAAAGAGAAA | AACATTCTTT | GATGATTCAT | CTTTAAATT  |
| 1121 | CTCAAAGCTC | GAATACGTAA | AATCTAATTA | ATATCAGCAT | AATCTCATTC | AGAGGCGGAG | CTAGCCTTGT | GTTAGGGGGT |

FIG. 9A

```
1201  ATTCAAACCT  TCTTTGACTG  AAAATTTTATT  ATTTATACA  TGTTTAAAAT  TACTTTTTAA  TGTATATATA  ATAGATATCA
1281  AATTCTTTAA  TTTGTATTTA  ATTCTATAAAT  ATTAAATTA  CTTTATTAAA  AATTCTAATT  CTGTCACTCG  TTCATTTCAT
1361  CACATTCTTG  ACGGTGATGG  TAGTGATAATT  ACATTGATT  GGAGCCACAT  GGGCCGCTAC  TTTTTAAAAA  GGATGAAACC
1441  TTGGAATGTA  GTGAATGTTG  AGTCTCAATAG  CTCAATCAC  GGACTCAACA  GCAAAGGTAA  GTGCCAAAAA  TCTGTCCTCT
1521  TTTTCCCTTC  TCCAATTGGA  GATACTGTCAC  CTTGGACAA  ATAATATTTG  AAAATTTTGG  CCTAAAAGTT  AGGTTTGGAG
1601  CCGTATGGTA  ATTTGATAAC  ACAAATTATTA  TATAATTGA  TATATCAAGT  ATATATATCC  AAAGTTGTCG  CATTCTTCGA
1681  TTCAATTTGT  TTCTCTCACT  AAAATTTTCAA  TTCACTTTT  TAAAAAAATCG  ATAAATTTT  AATATAACTT  TACATAACAT
1761  ATTCAAAATT  ACAAAAATAA  AGGATATTTT  ATATGTTTA  TTTTTAATGT  AAGATTAAAT  ATTTAGAATT  CTTTTTAAGA
1841  ACGGTACAAG  CAAATTAAAA  GAGAGAAGGTA  TATTAGTGG  GCCTATGTAT  CTTTGTATAC  ATATGCCTCT  CAAAGAGCTA
1921  CCTGATGAGT  CTATATATCT  TTGTTGATAGT  GATTAACA  ATTTATGTAT  GTACGTACTA  AGACATGTTA  AATAAGTACC
2001  TAGAGAAAGA  TTTTTGGAAA  AGTGAAAACAG  CAATAAAGA  AAAGTCATTT  AAACACTTTC  CAACAAACAT  TTGGTAATCG
2081  ATTTAATTA  CCCACTTAAA  CAAAACTATTT  GTACGTAAA  ATGTTTAAGT  AGAAAAGAGA  TTTTTTTTA  AAAAAAAAAG
2161  AAGGCAAGAG  GTCATATATC  TGACCCTTCCT  AATCCCCC  GCGTATAACA  CTTTCTTTT  TTTGTGTGT  GTATGTTCAG
2241  GAACATTTAT  ATTTTCTATT  TGAAATTTCTC  ATTAAGTCA  AATTCGAAAT  CTTTTAAATA  ATGTAGAAAA  ATCTCATTAT
2321  ATTTAACAAT  CCCACTTGAT  GAATTCCTAAA  CATTTTCTA  TAAAATAACA  CTAAATCTTT  AATTATACAT  ATTACATACC
2401  TAACTCAAGC  ATCTTGTCGG  TAAAAATCATT  AGAAAAGAA  TTGGAAATAG  GGAAATTCAT  AGACATATTT  TGGTTAGTAT
2481  CTTTGTCTAT  AAGAATGGGT  GTGTTAAAGAG  CTAGTGCCA  TAGTGTACCA  TTCTATTGGT  AGCATTTGGC  AAGAGTTATT
2561  CCCTCTCTCC  ATACCAATGG  AGAAGTTTAAT  CTTGCTAGA  GTCTTATTGT  TGCTTCTTCA  ACTTGGAACT  TTGTTCATTG
2641  CCCATGCATG  TCCTTATTGC  ATGTCCTTATT  GTCCATATC  CTCCTTCCAC  CCCAAAACAC  CCAAAATTGC  CTCCTAAGGT
```

FIG. 9B

| | | | | | | | |
|---|---|---|---|---|---|---|---|
| 2721 | GAAACCACCC | TCTACACAAC | CTCCACATGTG | AAACCACCT | TCTACCCCTA | AACACCCTAA | AGATCCTCCA | CATGTGAAGC |
| 2801 | CACCTTCTAC | CCCTAAACAA | CCACCATATGT | GAAACCACC | TACTACCCCT | AAACACCCTC | CACATGTTAA | ACCACCTTCC |
| 2881 | ACCCCTAAAC | ACCCTAAACA | CCCCCCACAAA | AACCATGCC | CTCCTCCATC | TCATCATGGT | CCTAAGCCAC | CAATTGTAAA |
| 2961 | ACCTCCACAT | GTACCAAGAC | CTCCTATAGTG | CATCCTCCT | CCCATTGTCT | CTCCACCTTC | CACACCTAAA | CCACCAAAAA |
| 3041 | CACCACCATT | CACTCCAAAA | CCACCATCACC | AATACCACC | TATTGTTTCA | CCCCCTATTG | TTTATCCACC | AATCACTCCA |
| 3121 | ACACCACCTA | TTGTCCATCC | ACCAGTCACTC | CAAAACCAC | CATCACCAAC | ACCTCCTATT | GTTTCACCCC | CCATTGTTTA |
| 3201 | TCCACCAATC | ACTCCAACAC | CACCTGTTGTG | TCACCTTCCA | ATCATTCCAA | CACCACCTAT | TGTCTCTCCA | CCTTTTGTCC |
| 3281 | CCAATCCTCC | CGTGGTAATA | CCACCACCCTA | CGTGCCAAG | TCCTCCGGTT | GTTACTCCAC | CCATAGTTCC | AACACCCCCT |
| 3361 | ACACCATGCC | CACCACCACC | ACCACCACCAG | CAATAATAC | CATCACCAAC | AGCACAACCA | ACTTGCCCCA | TTGATGCTCT |
| 3441 | CAAGCTAGGT | GCTTGTGTGG | ACGTGTTAGGA | GGACTAATC | CACATTGGAA | TCGGTGGAAG | TGCTAAGCAA | ACATGTTGTC |
| 3521 | CACTTCTAGG | AGGACTAGTA | GACTTGGATGC | AGCCATTTG | TCTTTGCACA | ACTATTAGAC | TCAAGCTCTT | TGACATTTCA |
| 3601 | ATCATTCTTC | CCATTGCTCT | ACAGGTTCTTA | TTGATGATT | GTGGCAAGTA | TCCACCCAAA | GACTTCAAGT | AAACATAAAC |
| 3681 | CTAAATCAAG | GTTTCCACTT | TTTCTCACTTT | CAATTATTA | CTCACTCCTA | CTCAATTTAT | GTGGTACAGT | GTCCTTCAAC |
| 3761 | AGTATTAGGC | CCAATTTTCT | TAGCTCGGAAT | TTTTTTAAA | TCTCTTTAAA | TATTTTGATT | TATACTACTT | TGACATTTCA |
| 3841 | TTTCATAAGT | ATAAATTTCA | TTTCATATATG | AATTCACGG | TCAAAAATTT | AAAGTTTATT | TAACCAATGC | CACATAACTT |
| 3921 | AGAACATACA | AATATCTTTT | TGATCAAGATT | TGGCAATTC | GTATACAATA | ATCTTTAGCA | AGTAATATGT | ATACCAACAT |
| 4001 | TATGTAAATAT | GATGCAGCAT | ATTAAACAGGA | CATTTGACT | GATACTGCCG | CATTGTCATA | AGTGAAGGCA | CAATAAATGT |
| 4081 | GTGAAAGTTC | AATTTCCATT | TTATCATGGCA | ATAAATTGA | GAAAACAAAG | GAGGGATATT | AATTAAGCTT | TAATTTGGCG |
| 4161 | TGTTTAATTA | GCTTTTGATT | AATGTACTGAA | TGTTGTATT | TACATTATTG | TTTTAGGGAA | ATACTAATGG | TATTTAGTAT |
| 4241 | AGTGGAGTATG | AATGCTGAT | TTGATTGTATG | AACACGAAT | GAATGAGGAA | AGAATCACCT | AATTTATCAC | GTGTTAATCT |

FIG. 9C

```
      (position 101) CTAGAATAAA TTAACTTGAT TTTGAGTCCA TGTATTAGA GATACATGTA TCTGGACATA
 161  TCAAAGTCTG ATAAAAATTCA TAATATTAAA ACATAGAGTG TCTTTAAGTA ATTAGCTCAT ACACTAGAAT GATTTTTGTA
 241  AGTTACACTT AAATAAATTG TTTTGGCCCA TGAGCCAACT GACCCCAATC AAGCCTCAAG GGCTTATATG AATCGAGTTT
 321  ATAAGCCCTA GTTTCAAATG AGCTTGAAAA ATTCTATCTC AACTATATCC AAATAATAGA TTGGATTGGA TCGAaTCCCA
 401  TGGGCTACGC ATTTTGATAG CTCTAGTTGT AACCCTAACT AATGATGAAA ATATTTTTGA CATGATATTT ATTTTATTAC
 481  CACAATTATT TTAATATTTA TTTTATACAT AATATATTTC TTATAAAATT ACTACACATA ATTGTCTGAT GACTGTAGAA
 561  GAGTAGTTGA CAAAATATTA TCGCAATGTC ATTGTTATTA TAGGTACAAA TTATTAAGTG AAAGTAGAAT ATAACGTGAA
 641  ATCGAATTAA AAAAATAATC AGATTGTAAT GAAATATATT TAGAGAGAAG TATTAAAGTA CCTATAAACT TGGCACAAAT
 721  TATTAGTTTT ATTTCTGTAC TATTGACAAC CTTAAAAACT ACTTGACTAA ATACACCTAG ATACACCTAA TTTTTTGTAG
 801  GAGCATGAAA CTCTTAATGA ATGGCCAAGA GAAGTGTTGA AAGCACCCCC AAACTTGATG AGAATTAGA GTGTATTTCA
 881  CCCATATTGC AAGATTGTAA GTGTATTTAA ATTTAGTTAA TCAATTAAAT AAATGTATTT TGAATTCCAA TAATTCAAGG
 961  ATGAAACAAA TAGTTCATAT TGAATTTAAA TGTTTTTTGA ATACTTCTTT TTTTCTCAAT ATTGACTAAC TAGTACAACC
 1041 AGGTTTGATT ATGATTTAGA TTTGTACCAC ATAAGATTAT TAAAGAGAAA AACATTCTTT GATGATTCAT CTTTTAAATT
 1121 CTCAAAGCTC GAATACGTAA AATCTAATTA ATATCAGCAT AATCTCATTC AGAGGCGGAG CTAGCCTTGT GTTAGGGGGT
 1201 ATTCAAACCT TCTTTGACTG AAAAATTTATT ATTTATACA TGTTTAAAAT TACTTTTTAA TGTATATATA ATAGATATCA
 1281 AATTCTTTAA TTTGTATTTA ATTCTATAAAT ATTAAATTA CTTTATTAAA AATTCTAATT CTGTCACTCG TTCATTTCAT
 1361 CACATTCTTG ACGGTGATGG TAGTGATAATT ACATTGATT GGAGCCACAT GGGCCGCTAC TTTTTAAAAA GGATGAAACC
 1441 TTGGAATGTA GTGAATGTTG AGTCTCAATAG CTCAATCAC GGACTCAACA GCAAAGGTAA GTGCCAAAAA TCTGTCCTCT
```

FIG. 10A

```
1521  TTTTCCCTTC  TCCAATTGGA  GATACTGTCAC  CTTGGACAA  ATAATATTTG  AAAATTTTGG  CCTAAAAGTT  AGGTTTGGAG
1601  CCGTATGGTA  ATTTGATAAC  ACAAATTATTA  TATAATTGA  TATATCAAGT  ATATATATCC  AAAGTTGTCG  CATTCTTCGT
1681  TTCAATTTGT  TTCTCTCACT  AAAATTTTCAA  TTCACTTTT  TAAAAAATCG  ATAAATTTTT  AATATAAACTT  TACATAAACAT
1761  ATTCAAAATT  ACAAAAATAA  AGGATATTTT  ATATGTTTA  TTTTTAATGT  AAGATTAAAT  ATTTAGAATT  CTTTTTAAGA
1841  ACGGTACAAG  CAAATTAAAA  GAGAGAAGGTA  TATTAGTGG  GCCTATGTAT  CTTTGTATAC  ATATGCCTCT  CAAAGAGCTA
1921  CCTGATGAGT  CTATATATCT  TTGTTGATAGT  GATTTAACA  ATTTATGTAT  GTACGTACTA  AGACATGTTA  AATAAGTACC
2001  TAGAGAAAGA  TTTTTGGAAA  AGTGAAAACAG  CAATAAAGA  AAAGTCATTT  AAACACTTTC  CAACAAACAT  TTGGTAATCG
2081  ATTTTAATTA  CCCACTTAAA  CAAAACTATTT  GTACGTAAA  ATGTTTAAGT  AGAAAAGAGA  TTTTTTTTA  AAAAAAAAAG
2161  AAGGCAAGAG  GTCATATATC  TGACCCTTCCT  TAAATCCCC  GCGTATAACA  CTTTCTTTTT  TTTTGTGTGT  GTATGTTCAG
2241  GAACATTTAT  ATTTCTATT  TGAAATTTCTC  ATTAAGTCA  AATTCGAAAT  CTTTTAAATA  ATGTAGAAAA  ATCTCATTAT
2321  ATTAACAAT  CCCACTTGAT  GAATTCCTAAA  CATTTTCTA  TAAAATAACA  CTAAATCTTT  AATTATACAT  ATTACATACC
2401  TAACTCAAGC  ATCTTGTCGG  TAAAAATCATT  AGAAAAGAA  TTGGAAATAG  GGAAATTCAT  AGACATATTT  TGGTTAGTAT
2481  CTTTGTCTAT  AAGAATGGGT  GTGTTAAAGAG  CTAGTGCCA  TAGTGTACCA  TTCTATTGGA  AGCATTTGGC  AAGAGTTATT
2561  CCCTCTCTCC  ATACCAATGG  AGAAGTTTAAT  CTTGCTAGA  GTCTTATTGT  TGCTTCTTCA  ACTTGGAACT  TTGTTCATTG
2641  CCC
```

FIG. 10B

```
(position 943)  AATTCCAA   TAATTCAAGG
 961  ATGAAACAAA  TAGTTCATAT  TGAATTTAAA  TGTTTTTTGA  ATACTTCTTT  TTTTCTCAAT  ATTGACTAAC  TAGTACAACC
1041  AGGTTTGATT  ATGATTTAGA  TTTGTACCAC  ATAAGATTAT  TAAAGAGAAA  AACATTCTTT  GATGATTCAT  CTTTTAAATT
1121  CTCAAAGCTC  GAATACGTAA  AATCTAATTA  ATATCAGCAT  AATCTCATTC  AGAGGCGGAG  CTAGCCTTGT  GTTAGGGGGT
1201  ATTCAAACCT  TCTTTGACTG  AAAATTTTATT ATTTATACA   TGTTTAAAAT  TACTTTTTAA  TGTATATATA  ATAGATATCA
1281  AATTCTTTAA  TTTGTATTTA  ATTCTATAAAT ATTAAAATTA  CTTTATTAAA  AATTCTAATT  CTGTCACTCG  GGATGAAACC
1361  CACATTCTTG  ACGGTGATGG  TAGTGATAATT ACATTGATT   GGAGCCACAT  GGGCCGCTAG  TTTTTAAAAA  GGATGAAACC
1441  TTGGAATGTA  GTGAAATGTTG AGTCTCAATAG CTCAATCAC   GGACTCAACA  GCAAAGGTAA  GTGCCAAAAA  TCTGTCCTCT
1521  TTTTCCCTTC  TCCAATTGGA  GATACTGTCAC CTTGGACAA   ATAATATTTG  AAAATTTTGG  CCTAAAAGTT  AGGTTTGGAG
1601  CCGTATGGTA  ATTTGATAAC  ACAAAATTATTA TATAATTGA  TATATCAAGT  ATATATATCC  AAAAGTTGTCG CATTCTTCGT
1681  TTCAATTTGT  TTCTCTCACT  AAAATTTTCAA TTCACTTTT   TAAAAAATCG  ATAAATTTTT  AATATAACTT  TACATAACAT
1761  ATTCAAAATT  ACAAAAATAA  AGGATATTTT  ATATGTTTA   TTTTTAATGT  AAGATTAAAT  ATTTAGAATT  CTTTTTAAGA
1841  ACGGTACAAG  CAAATTAAAA  GAGAGAAGGTA TATTAGTGG   GCCTATGTAT  CTTTGTATAC  ATATGCCTCT  CAAAGAGCTA
1921  CCTGATGAGT  CTATATATCT  TTGTTGATAGT GATTTAACA   ATTTATGTAT  GTACGTACTA  AGACATGTTA  AATAAGTACC

FIG. 11A
```

| | | | | | | |
|---|---|---|---|---|---|---|
| 2001 | TAGAGAAAGA | TTTTTGGAAAA | AGTGAAAACAG | CAATAAAGA | AAAGTCATTT | AAACACTTTC | CAACAAAACAT | TTGGTAATCG |
| 2081 | ATTTTAATTA | CCCACTTAAA | CAAAACTATTT | GTACGTAAA | ATGTTTAAGT | AGAAAAGAGA | TTTTTTTTTA | AAAAAAAAAG |
| 2161 | AAGGCAAGAG | GTCATATATC | TGACCCTTCCT | TAAATCCCC | GCGTATAACA | CTTTCTTTTT | TTTTGTGTGT | GTATGTTCAG |
| 2241 | GAACATTTAT | ATTTTCTATT | TGAAATTTCTC | ATTAAGTCA | AATTCGAAAT | CTTTTAAATA | ATGTAGAAAA | ATCTCATTAT |
| 2321 | ATTTAACAAT | CCCACTTGAT | GAATTCCTAAA | CATTTTCTA | TAAAATAACA | CTAAATCTTT | AATTATACAT | ATTACATACC |
| 2401 | TAACTCAAGC | ATCTTGTCGG | TAAAAATCATT | AGAAAAGAA | TTGGAAATAG | GGAAATTCAT | AGACATATTT | TGGTTAGTAT |
| 2481 | CTTTGTCTAT | AAGAATGGGT | GTGTTAAAGAG | CTAGTGCCA | TAGTGTACCA | TTCTATTGGT | AGCATTTGGC | AAGAGTTATT |
| 2561 | CCCTCTCTCC | ATACCAATGG | AGAAGTTTAAT | CTTGCTAGA | GTCTTATTGT | TGCTTCTTCA | ACTTGGAACT | TTGTTCATTG |
| 2641 | CCC | | | | | | | |

FIG. 11B

```
1     ATGCATCCCA  AATAGGCGAG  TGAGATGGAA  GGGAGGCAAT  GACACGAAAT  TTGTCTATGT  GTCCTAGATA  TGTAAGAATT
81    CACTGATATA  TTGAGTGTAT  CTAGAATAAA  TTAACTTGAT  TTTGAGTCCA  TGTATTTAGA  GATACATGTA  TCTGGACATA
161   TCAAAGTCTG  ATAAAATTCA  TAATATTAAA  ACATAGAGTG  TCTTTAAGTA  ATTAGCTCAT  ACACTAGAAT  GATTTTTGTA
241   AGTTACACTT  AAATAAAATTG  TTTTGGCCCA  TTTTGGCCCA  GACCCCAAAT  AAGCCTCAAG  GGCTTATATG  AATCGAGTTT
321   ATAAGCCCTA  GTTTCAAATG  AGCTTGAAAA  ATTCTATCTC  AACTATATCC  AAATAATAGA  TTGGATTGGA  TCGAaTCCCA
401   TGGGCTACGC  ATTTTGATAG  CTCTAGTTGT  AACCCTAACT  AATGATGAAA  ATATTTTTGA  CATGATATTT  ATTTTATTAC
481   CACAATTATT  TTAATATTTA  TTTTATACAT  AATATATTTC  TTATAAAATT  ACTACACATA  ATTGTCTGAT  GACTGTAGAA
561   GAGTAGTTGA  CAAAATATTA  TCGCAATGTC  ATTGTTATTA  TTATTAAGTG  TATTAAAGTA  AAAGTAGAAT  ATAACGTGAA
641   ATCGAATTAA  AAAAAATAATC  AGATTGTAAT  GAAATATTAT  TAGGTACAAA  TATTAAAGTA  CCTATAAACT  TGGCACAAAT
721   TATTAGTTTT  ATTTCTGTAC  TATTGACAAC  CTTAAAAACT  ACTTGACTAA  CTAAACCTAG  ATACACCTAA  TTTTTTGTAG
801   GAGCATGAAA  CTCTTAATGA  ATGGCCAAGA  GAAGTGTTGA  AAGCACCCCC  AAACTTGATG  AGAATTTAGA  GTGTATTTCA
881   CCCATATTGC  AAGATTGTAA  GTGTATTTAA  ATTTAGTTAA  TCAATTAAAT  AAATGTATTT  TGAATTCCAA  TAATTCAAGG
961   ATGAAACAAA  TAGTTCATAT  TGAATTTTAA  TGTTTTTTGA  ATACTTCTTT  TTTTCTCAAT  ATTGACTAAC  TAGTACAACC
1041  AGGTTTGATT  ATGATTAGA   TTTGTACCAC  ATAAGATTAT  TAAAGAGAAA  AACATTCTTT  GATGATTCAT  CTTTTAAATT
1121  CTCAAAGCTC  GAATACGTAA  AATCTAATTA  ATATCAGCAT  AATCTCATTC  AGAGGCGGAG  CTAGCCTTGT  GTTAGGGGGT
1201  ATTCAAACCT  TCTTTGACTG  AAAATTTTATT  ATTTATACA   TGTTTAAAAT  TACTTTTTAA  TGTATATATA  ATAGATATCA
```

FIG. 12A

```
1281  AATTCTTTAA  TTTGTATTTA  ATTCTATAAAT  CTTTATTAAA  AATTCTAATT  CTGTCACTCG  TTCATTTCAT
1361  CACATTCTTG  ACGGTGATGG  TAGTGATAATT  ACATTGATT   GGGCCGCTAC  TTTTTAAAAA  GGATGAAACC
1441  TTGGAATGTA  GTGAATGTTG  AGTCTCAATAG  CTCAATCAC   GCAAAGGTAA  GTGCCAAAAA  TCTGTCCTCT
1521  TTTTCCCTTC  TCCAATTGGA  GATACTGTCAC  CTTGGACAA   AAAATTTTGG  CCTAAAAGTT  AGGTTTGGAG
1601  CCGTATGGTA  ATTTGATAAC  ACAAATTATTA  TATAATTGA   ATATATATCC  AAAGTTGTCG  CATTCTTCGT
1681  TTCAATTTGT  TTCTCTCACT  AAAATTTTCAA  TTCACTTTT   (2079) :CG
2081  ATTTAAATTA  CCCACTTAAA  CAAAACTATTT  GTACGTAAA   AGAAAAGAGA  TTTTTTTTTA  AAAAAAAAAG
2161  AAGGCAAGAG  GTCATATATC  TGACCCTTCCT  TAAATCCCC   CTTTCTTTT   TTTTGTGTGT  GTATGTTCAG
2241  GAACATTTAT  ATTTCTATT   TGAAATTTCTC  ATTAAGTCA   AATTCGAAAT  ATGTAGAAAA  ATCTCATTAT
2321  ATTTAACAAT  CCCACTTGAT  GAATTCCTAAA  CATTTTCTA   TAAAATAACA  AATTATACAT  ATTACATACC
2401  TAACTCAAGC  ATCTTGTCGG  TAAAAATCATT  AGAAAAGAA   TTGGAAATAG  AGACATATTT  TGGTTAGTAT
2481  CTTTGTCTAT  AAGAATGGGT  GTGTTAAAGAG  CTAGTGCCA   TAGTGTACCA  AGCATTTGGC  AAGAGTTATT
2561  CCCTCTCTCC  ATACCAATGG  AGAAGTTTAAT  CTTGCTAGA   GTCTTATTGT  ACTTGGAACT  TTGTTCATTG
2641  CCC
```

FIG. 12B

```
   1 GGCACTTGCC TTTTTCGTAA CTATCCAACT CACATCACAA ATTGCTATTC CTTCCACGAT TTCAACCAGT
  81 AGATCTCACT CCAGCATGGA GCCAGATAAA CCTATTCGAG GGGATCCGAT TTGCTTTTGC AATCTATAGC CGTGACTATA
 161 GCAAACCCCT CCTGCATTTC CAGAAACGAT CAGAAACGAT AGTGCTAGAT ACTCTCCACC GATATATATA
 241 CTTAAACAAC TAGCTGAGCT CTTGAAGAAC AAAGTCTGCT ATCATCCTCC AGTCAGCCGG ATCTGGCTCG
 321 AGAAAACGAC CAACATGTAT TTGTCTATCT TTCTCGCGAG AAGATGCAGA GGAACAATCC ATTACATTTG
 401 GAATGGAGGC CGTGCTGGCG ACAACGATTC AACCATATCG GAGCGAGCTC AGATGCTCCG TGTTCACAAC
 481 CTTGCTTGGC CGCACAGCCG CCTGATTTAG AATGCTTCAT GCCCTCCAGG GCAAGTTCCT TGTTCATTCA
 561 CTTGCTGGAG TTAAAAGTGA CCAACGTTTA CGGGAGAGAG GTAGCTTGCA CGCCATTTTC CCTTCTTTCT GCGGCGAGGG ACTGAAAACC
 641 GCCCCTATGA TGTTGTAGCT TGCGGCACCA CACAATTCAC CAAAAATGCC CTCGGGATAT CACGTCCGC CGCCCTCCTCA
 721 CCGGAGCCAG ACCTAAACCT GCGACTCTCG GGGCCTGATC AGGAAGGCGA GGAGGGCGTC ATGAAGCCTG CTGCAGTAAA
 801 CCTGAAGAAA GAAGCCTAAA GCCGACTTGA ACTCCCCCTG CAGGCAACCT TTATCTATAA GTTTGTCATA AGTTCTATGT
 881 ACCCTCCCGC AGTCTGTGAC ACAGAACCTT GGGAGTTGTA GCGTACGTTA TAATGTGTTG ACCTATTTTC TTGTACTAAA
 961 TATTTTCTTC TGTGTTGATC CTGCTGCTGA ATTTTGCCAA AAACAGCACA TGCTCATATG ACTATCTAAT CTACTACACA
1041 TATATTGCAG TATCAACAAC AACGACACAC CTGGACTTAT AATATTATAG TTCAACAGTA CATTGACAT AAAACATTT
1121 CACGACATTA CACAAAACGT CTAAAGTAC GTTAAAGTAC AATATTAATA AAACAGGACA ATCGCGCCAT GGCTCGCAGC
1201 TTATTTAAC TTAACAGAAC ATATTCGATA TCATCTCCGG CGTGGAAATG CGCCAGCCAC GTGCGTATTA
1281 ATCCCGTAGG TTTGTTTCGA AATGCGTATT AATCCCGTAG GTCTGAATTT TCACGTCCGG CGACAAAGGG TCCCTTCGCA
1361 GCAACTCGCG GGTCGTTGAA CGTCCCGGTC GGGCTTGGGA AGTCATGGCC AAAGGAGTGG TGCTCAGATT GGCTGGCTCA
1441 GCAAGATGGT CGCGTTCGCC CGGGATACC CGTTTGGCCT TCCTCTTGGC CTTTGCACGC CTAACAAGCT T
```

FIG. 13

| Transgenic plant (Ro) | PCR (nptII) | Seed bearing phenotype | Ratio of Kan^r (in R_1 seedlings) |
|---|---|---|---|
| MPB-4-Ro | + | All fruits seedless (>40 fruits)# | ~3/4 |
| MPB-12-Ro | + | Most fruits seedless, a few seeded | ~3/4 |
| MPB-13-Ro | + | Most fruits seedless, a few seed | ~16/17 |

Complete seedlessness in all fruits developed on 8 plants developed from cuttings of the MPB-4 regenarated plant.

FIG. 14A

| Transgenic plant (R₁) | No. Kanr plants tested | Seed bearing phenotype |
|---|---|---|
| MPB-12-R₁ | 7 | In all of the plants (MPB-12-R₁-1,2*,3,4,5*,6,7) most of the fruits were seedless and few (2-4 fruits) were seeded (ranging 2-40 seeds/fruit). |
| MPB-13-R₁ | 7 | In 2 plants (MPB-13-R₁-1,5) all fruits were seedless. |
| | | In 2 plants (MPB-13-R₁-4*,6) most of the fruits were seedless, several fruits beared a few seeds (10<seeds), few fruits beared 10-20 seeds. |
| | | In 2 plants (MPB-13-R₁-2,6*) approx. half of the fruits were seedless, and half were seeded (ranging 5-20 seeds/fruit). |
| | | In 1 plant (MPB-13-R₁-3*) all the fruits were seeded (ranging 5-20 seeds/fruit). |

* Designates R₁ plant which is heterozygote according to segragation of its progenies for sensitivity to Kan in the germination medium.

FIG. 14B

| Line | Sample size[1] | Fruits/plant[2] | Weight (g) | No. locules | °Brix | seeds/fruit | median & |
|---|---|---|---|---|---|---|---|
| -1 | nP1=5; nFr=14 | 9.0+0.543 a | 36.7+2.60 bc | 4.2+0.33 a | 7.38+0.144 a | 68+5.17 a | 65 (40-100) |
| MPB-12.5-R2 | nP1=3; nFr=23 | 8.2+0.355 a | 35.3+2.06 bc | 3.9+0.31 a | 7.29+0.096 a | 19+11.48 b | 20 (0.40) |
| MPB-13.3-R2 | nP1=2; nFr=15 | 11.3+0.797 b | 30.7+1.17 c | 3.7+0.30 a | 7.01+0.127 a | 27+3.74 b | 30 (1-50) |
| MPB-13.4-R2 | nP1=2; nFr=7 | 3.3+0.522 c | 42.5+2.99 ab | 5.0+0.72 a | 7.71+0.380 a | 10+4.36 b | 10 (0-30) |
| F value[3] | | 22.278 | 3.333 | 1.5435 | 2.591 | 40.88 | |
| P value[3] | | <0.0001 | 0.026 | 0.216 | 0.0621 | <0.0001 | |

1 nP1= number of plants sampled, nFr=total number of fruits sampled from the given number of plants, fruits were collected between 14-30 June 1995.

2 The total number of fruits on the plant when sampled (onlly fruits greater than 15 mm were counted).

3 F and P values for the data presented in the column, Anova test was performed using Graphpad Instat 2.01 programme for MacIntosh, including Turkey test for analysis of all pairs within the column.

FIG. 15

METHOD FOR THE INDUCTION OF GENETIC PARTHENOCARPY IN PLANTS

FIELD OF THE INVENTION

The present invention concerns a method for production of parthenocarpic plants and more particularly it is a method for producing genetic parthenocarpy.

BACKGROUND OF THE INVENTION

Fruit setting and development normally depend on successful fertilization. In tomato and many other species, a major limiting factor for fruit setting is the extreme sensitivity of the pollen production to moderately high or low temperatures and inadequate humidity (Picken 1984). Parthenocarpy, which is the ability to set seedless fruits, enables to circumvent these environmental constraints on fruit production. Consequently, in many fruit bearing plants parthenocarpy is of considerable economic significance.

Parthenocarpy may either be artificially induced in normal plants or may occur naturally as the result of a genetic trait. Genetic parthenocarpy may be obligatory or facultative. In the former seeds are never formed. In facultative parthenocarpy seedless fruit is produced when environmental conditions are unfavorable for pollination and fertilization. However, when fertilization does occur seeded fruits are formed, which enables reproductive propagation of the facultative partienocarpic plants.

Parthenocarpy is discussed in various scientific articles, such as:

Abad M, Monteiro A A (1989) The use of auxins for the production of greenhouse tomatoes in mild-winter conditions: A review. Sci Hort 38: 167–192.

Gustafson F G (1939a) The cause of natural parthenocalpy. Amer J Bot 26: 135–138.

Gustafson F G (1939b) Auxin distribution in fruits and its significance in fruit development. Amer J Bot 26: 189–194.

Ho L C, Hewitt J D (1986) Fruit development. In: The Tomato Crop. A Scientific Basis for Improvement. (Athemon JR and Rudich J, Eds), Chapman and Hall, London, New York. Pp. 201–239.

Nitsch J P (1970) Hormonal factors in growth and development. In: The biochemistry of fruits and their products (AC Hulme ed). Vol 2, Academic Press, London. Pp.428–47.

Picken A J (1984) A review of pollination and fruit set in the tomato (*Lycopersicon esculentum* Mill .) J Hort Sci 59: 1–13.

Varga A, Bruinsma J (1986) Tomato. In: CRC Handbook of Fruit Set and Development (Monselise SP, ed.) CRC Press Inc. Boca Raton, Fla. Pp. 461–481. In the tomato, the most effective treatments for induction of parthenocarpy utilize auxins, synthetic auxins or auxin transport inhibitors (reviewed by Ho and Hewitt 1986, Varga and Bruinsma 1986, Abad and Monteiro 1989). However, this treatment is very laborious since the auxin has to be applied to each truss separately, to avoid the adverse effects characteristic to auxin application to the whole plant.

Auxin also appears to play a role in genetic (natural) parthenocarpic fruit set. For example, Gustafson (1939a,b) found that auxin concentrations in ovaries of parthenocarpic orange, lemon and grape varieties were significantly higher than in seeded varieties. Based on similar data, Nitsch (1970) suggested that natural parthenocarpy is related to the ability of seedless varieties to establish a threshold concentration of hormones required for fruit set at anthesis.

Several genes which control the effect of auxin in plants are known in the art.

One such gene, for example, is the rolB gene which is included in TL-DNA of the *Agrobacterium rhizogenes* agropine-type Ri-Plasmid. (Chilton M D, Tepfer D A, Petit A, David C, Casse-Delbart F, Tempe J (1982) *Agrobacterium rhizogenes* inserts T-DNA into the genome of host plant root cells. Nature 295:432–434. Spano L, Pomponi M, Constantino P, van Sloteren G M S and Tempe J (1982) Identification of T-DNA in the root-inducing plasmid of the agropine type *Agrobacterium rhizogenes* 1855. Plant Mol Biol 1: 291–300, White F F, Ghidossi G, Gordon M P, Nester E W (1982) Tumor induction by *Agrobacterium rhizogenes* involves the transfer of plasmid DNA to the plant genome. Proc. Natl Acad Sci USA 79:3193–3197, Willmitzer L, Sanchez-Serrano J, Buschfeld E, Schell J (1982) DNA from *Agrobacterium rhizogenes* is transfered to and expressed in axenic hairy root plant tissues. Mol Gen Genet 186:16–22., Peterson SG, Stummann B M, Olsen P, Henningsen K W (1989) Structure and function of root-inducing (Ri) plasmids and their relation to tumor-inducing (Ti) plasmids. Physiol Plant 77:427–435).

Transgenic plants expressing the rolB gene under its native or constitutuve promoter manifest several syndromes characteristics of auxin toxicity, such as leaf abnormalities, increased stigma and flower size, heterostyly and increased formation of adventitious roots on the stem (Schmulling T, Schell J, Spena A (1988) Single genes from *Agrobacterium rhizogenes* influence plant development EMBO J 7:2621–2629). van Altvorst et al. (van Alvorst A C, Bino R J, van Dijk A J, Lambers A M J, Lindout W H, van der Mark F, Dons J J M (1992) Effects of the introduction of *Agrobacterium rhizogenes* rol genes on tomato plant and flower development. Plant Sci 83:77–85.) described the phenotypic effects of the various rol genes in transgenic tomato, however, they did not report parthenocarpic fruit development when the rolB gene was inserted.

SUMMARY OF THE INVENTION

The present invention provides an improved method for the production of genetic parthenocarpy in plants.

There is thus provided in accordance with a preferred embodiment of the present invention a method for the production of genetic parthenocarpy in plants which include the steps of providing a cassette including a DNA sequence coding for modulation of auxin effects in plants, and a promoter specific for the ovary between anthesis and early fruit development to control the DNA sequence, and introducing the cassette into a plant.

Preferably the method also includes the step of screening the plant for either facultative or obligatory parthenocarpic characteristics.

In accordance with a preferred embodiment of the present invention the step of introducing includes the steps of transformation of plant material, and regeneration of transformed plants.

In accordance with another preferred embodiment of the present invention the plant material includes seed derived cotyledons.

In accordance with yet another preferred embodiment of the present invention the step of transformation includes the steps of providing a plasmid incorporating the cassette, introducing the plasmid into *Agrobacterium tumerfaciens*, and incorporating the plasmid into the plant material by co-cultivation with the *A. tumerfaciens*, including the plasmid.

In accordance with still another preferred embodiment of the present invention the DNA sequence coding for modulation of auxin effects in plants, includes the sequences of the rolB gene.

In accordance with a further preferred embodiment of the present invention the step of screening includes growing the plant to produce fruit, and examining the fruit for seed production under fertility permissive conditions.

In accordance with still a further preferred embodiment of the present invention the step of screening includes growing the plant to produce fruit, and examining the fruit for seed production under fertility restrictive conditions.

Preferably the method also includes the step of screening the plant for either facultative or obligatory parthenocarpic characteristics.

In accordance with a preferred embodiment of the present invention the tomato plant includes the fruit of the tomato plant.

DESCRIPTION OF THE DRAWINGS

The present invention will be understood and appreciated more fully from the following detailed description taken in conjugation with the drawings and tables in which:

FIG. 9—Seq ID1 shows the sequence of the TPRP-F1 genomic clone, including 2643 bp of the promoter region. The sequence of the promoter region extending from 1–2483 was not published earlier. The sequence extending from 2484–4320 was published earlier (Salts Y, Kenigsbuch D, Wachs R, Gruissem W, Barg R (1992) DNA sequence of the tomato fruit expressed proline-rich protein gene TPRP-F1 reveals an intron within the 3'-untranslated transcript. Plant Mol Biol 18:407–409). The ATG codon printed in bold letters (position 2644–2646) is the translation initiation codon used for the GUS promoter expression analysis. The underlined bold G (position 2235) is the transcription initiation site (unpublished data).

FIG. 10—Seq ID2: shows the sequence of the TPRP-F1 promoter included in the binary plasmid pGB18rolB (FIG. 8). The sequence corresponds to 101–2643 in Table 1.

FIG. 11—Seq ID3: shows a shorter promoter that confers ovary and embryo specificity (From 943–2643 in Table 1)

FIG. 12—Seq ID4: shows an alternative combination of sequence from the TPRP-F1 promoter that confers ovary and developing embryo specificity (From 1–1728 fused to 2079–2643, Table 1)

FIG. 13—Seq ID5: shows the sequence of the rolB gene included in the binary vector pGB18rolB (see FIG. 5). The sequence is that presented in Slightom et al (Slightom J L, Durand-Tardif M, Jouanin L, Tepfer D (1986). Nucleotide sequence analysis of TL-DNA of *Agrobacterium rhizogenes* Agropine type plasmid. Identification of open reading frames. J. Biol Chem 261:108–121).

Figure 1:
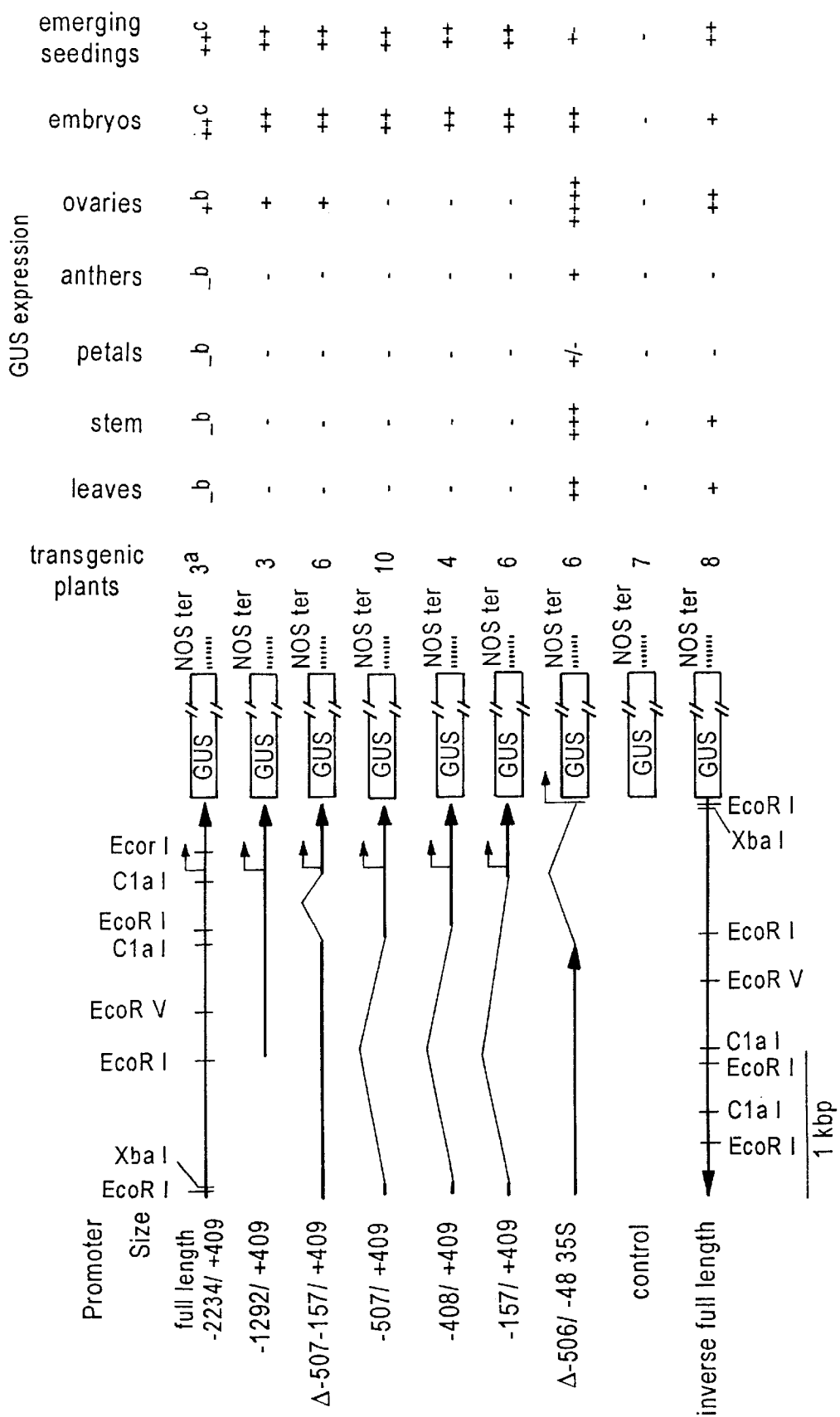
FIG. 1 is a diagrammatic analysis of GUS expression in transgenic plants harboring various deletions of the TPRP-F1 promoter sequence; a) this column a indicates the number of independent transgenic plants. b) the evaluation of GUS expression is based on data obtained from fluorometric assay with 4MU. (++++ indicates extremely high fluorescence, +++ very high fluorescence, ++ high fluorescence, + intermediate high, +/− intermediate low, − no fluorescence). c) GUS expression evaluation based on histochemical assay with X-Gluc. (++ indicates high color developed within 2 hr., + high color developed upon overnight incubation, +/− faint color developed upon overnight incubation, − no color developed upon overnight incubation). In contrast Δ −506/−46 35S the minimal −46 CaMV-35S promoter is installed in front of the GUS-ORF (open reading frame). In all other plasmids the 5'UTR (untranslated region) of the TPRP-F 1 promoter is retained.
Figure 2:
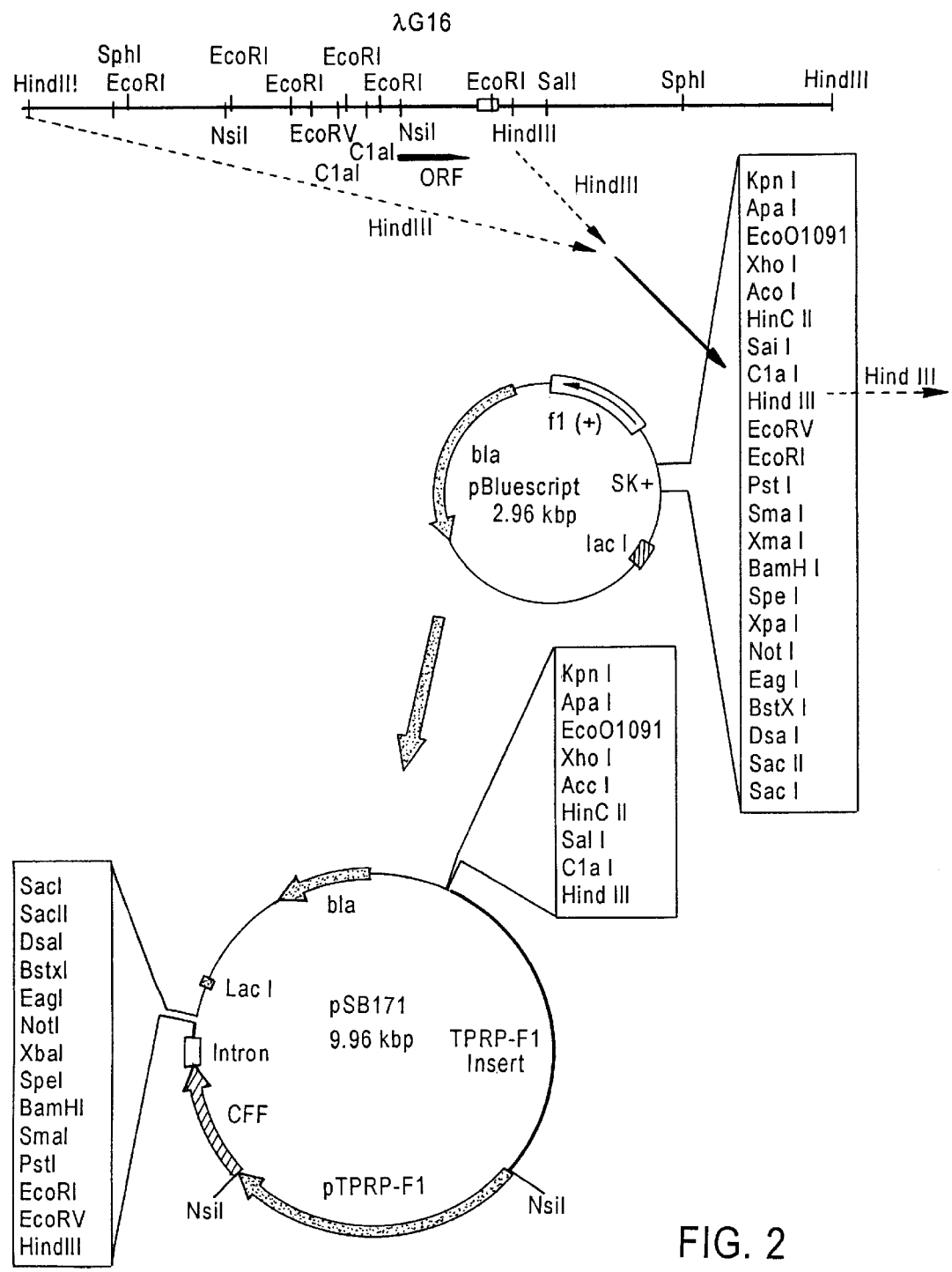
FIG. 2 is a diagram of the construction of plasmid pSB171; The 7Kbp HindIII fragment of λG16 was inserted into the HindIII site of plasmid pBluescript SK+.

The translation initiation codon (position 40) is presented in bold letters.

FIG. 14–Table 6: shows seed bearing phenotype of the various parthenocarpic transgenic plants ($R_0$) and their progenies ($R_1$).

FIG. 15—Table 7: shows the analysis of characteristics of fruits developed on $R_2$ transgenic plants and the parental line MP-1. Within columns values followed by common letters do not differ significantly at P=0.05.

In table 7:
1) nP1=number of plants sampled, nFr=total number of fruits sampled from the given number of plants, fruits were collected between 14–30 June 1995.
2) The total number of fruits on the plant when sampled (only fruits greater than 15 nun were counted).
3) F and P values for the data presented in the column, Anova test was performed using Graphpad Instat 2.01 program for MacIntosh, including Turkey test for analysis of all pairs within the column.

DETAILED DESCRIPTION OF THE PREFERRED EMBODIMENTS

Reference is now made to the method involved in the production of genetic parthenocarpy in plants. The method for production includes providing a cassette including a DNA sequence coding for modulation of auxin effects, and a promoter specific for the ovary between anthesis and early fruit production to control the DNA sequence, introducing the cassette into a plant, and screening the plant for parthenocarpic characteristics.

Materials & Methods

Bacterial strains and cultures: The *E. Coli* strain DH5α (Raleigh E A, Lech K, Brent R. (1989) In Current protocols in molecular biology (Eds. Ausubel F M et al. Publishing associates and Wiley Interscience NY, Unit 1.4) served for all the plasmid construction steps, and strain SM10 (Simon R, Preifer U, Puhler A (1983) A broad host mobilization system for in vitro genetic engineering: transposon mutagenesis in Gram-negative bacteria. Bio/technology 1:784–791)

served for conjugation of the plasmids into *Agrobacterium tumefaciens*. PCR, DNA and RNA analysis, and recombinant plasmids construction were performed according to established procedures: (Ausubel F M, Kingsten R E, Moore D D, Smith J A, Seideman J G, Struhl K. (1988) Current protocols in molecular biology Wiley InterScience, Sambrook J, Fritsch E F, Maniatis T (1989). Molecular Cloning. A laboratory manual. Second edition. Cold Spring Harbor Laboratory Press, USA.)

EXAMPLE 1

Detailed analysis of the ovary and early fruit specific TPRP-F1 promoter

The promoter of the TPRP-F1 gene was isolated following the characterization of the TPRP-F1 gene as an ovary and early fruit specific one, and following sequencing of the gene's coding region (Salts Y, Wachs R, Gruissem W, Barg R (1991). Sequence coding for a novel proline-rich protein preferentially expressed in young tomato fruit. Plant Mol Biol 17: 149–150 and Salts et al 1992). Later on a genomic clone was isolated. The sequence of the genomic clone including putative promoter region extending 2643 bp 5' to the translation initiation codon is presented in Seq ID1. The sequenced of the coding region, including 160 bp 5' to the translation initiation codon (position 2643 in Seq ID1) was published previously (Salts et al. 1992), while the sequence extending between 1–2644 (Seq ID1) was not published.

In the present invention, the ATG codon (starting at position 2644 in Seq ID1) served as the initiation codon of all the constructs containing the TPRP-P1 gene promoter used in the described experiments.

A preliminary functional analysis of the promoter was performed by fusion of various deletions of the putative promoter sequence to the reporter gene uidA (GUS), and analysis of GUS expression (Jefferson R A, Kavanagh T A, Bevan M W (1987) GUS Fusions: β-glucuronidase as a sensitive and versatile gene fusion marker in higher plants EMBO J 6:3901–3907) in stable transgenic tomato plants. The results of the preliminary analysis were briefly reported (Carmi N, Barg R, Salts Y (1994) Expression of a tomato young fruit specific proline-rich coding gene. In Abstracts of 4th International Congress of Plant Molecular Biology. Amsrterdam (Abs. 538)). Primer extension analysis indicated that the transcript of the construct includes 408 bp of untranslated leader sequence. A detailed analysis of the promoter region of the TPRP-F1 gene was performed including additional deletions and testing GUS expression in more organs and at additional developmental stages. The results of this analysis are summarized in FIG. 1.

The main findings of this analysis are:

1. The sequence extending 2542 bp 5' to the translation initiation codon (Seq ID2) served as the promoter to which the rolB gene was fused in the chimeric gene. (see also FIGS. 2–8), Based on this analysis (see FIG. 1), a sequence extending only 1701 bp 5' to the translation initiation codon is sufficient to drive ovary and developing embryo specific expression of the rolB gene (Seq ID3)
2. The results of this analysis also indicate that a promoter sequence extending 564 bp 5' to the translation initiation codon fused to a sequence extending from 915 to 2643 bp 5' to the translation initiation codon confers specificity to the ovary and young fruits and to developing embryos (Seq ID4). And this sequence too can be used to drive the expression of the rolB specifically in the fruit, leading to parthenocarpy without the adverse effects of expression in other organs and additional developmental stages.

Construction of the chimeric gene TPRP-F1::rolB
Construction of the plasmid pSB171

The recombinant plasmid pSB171 (FIG. 2) was obtained by subcloning the genomic 7kbp λG16 Hind III fragment into the Hind III site of pBluescript SK$^+$.

Construction of the plasmid pBSN28

Figure 3:
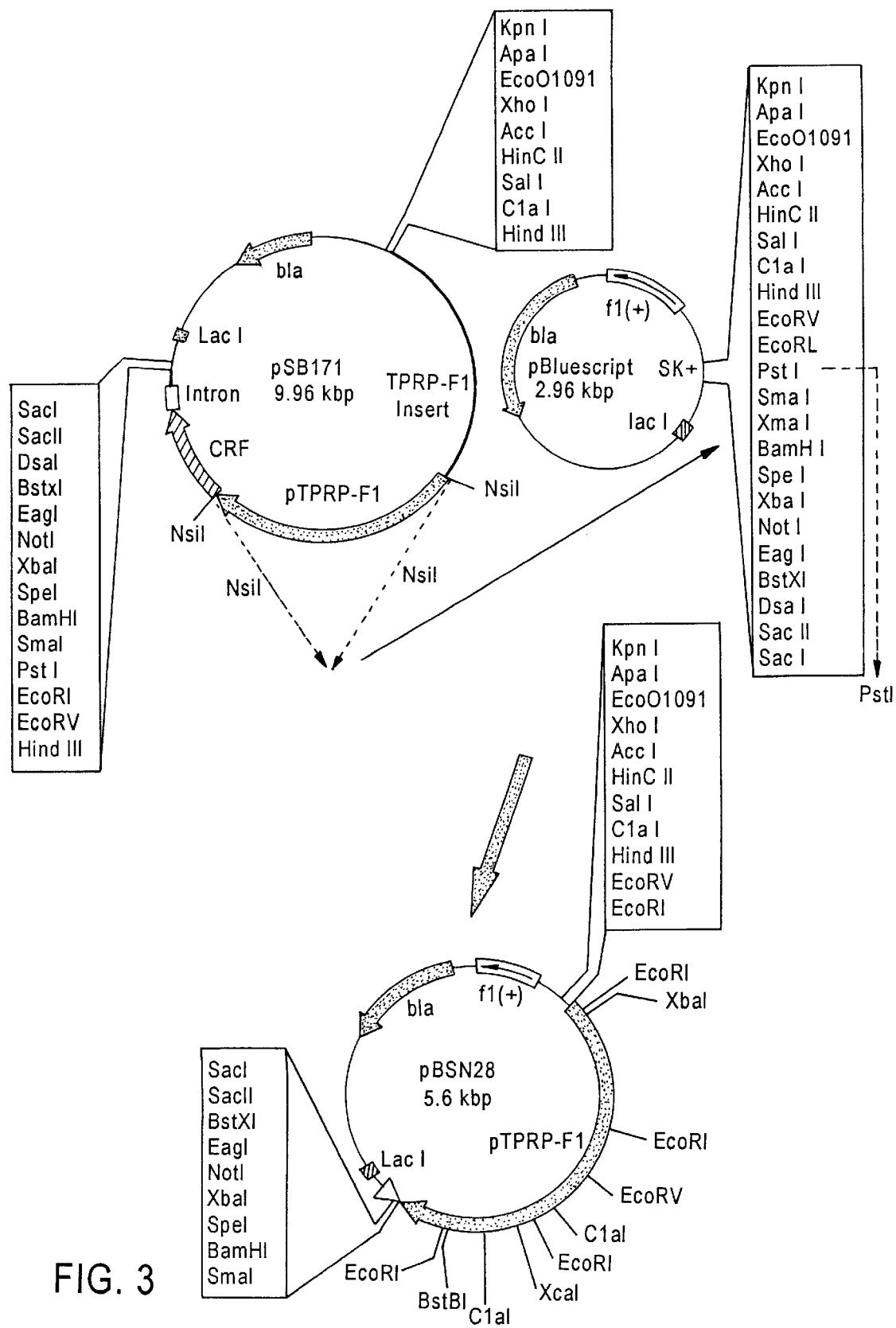
FIG. 3 is a diagram of the construction of pSBN28; The NsiI fragment of pBS171 was inserted into the Pst I site of pBluescript.

The Nsi I internal fiagment of plasmid pSB171 was isolated and subcloned into the Pst I restriction site of pBluescript (FIG. 3).

Construction of the plasmid pBSN33

Figure 4:
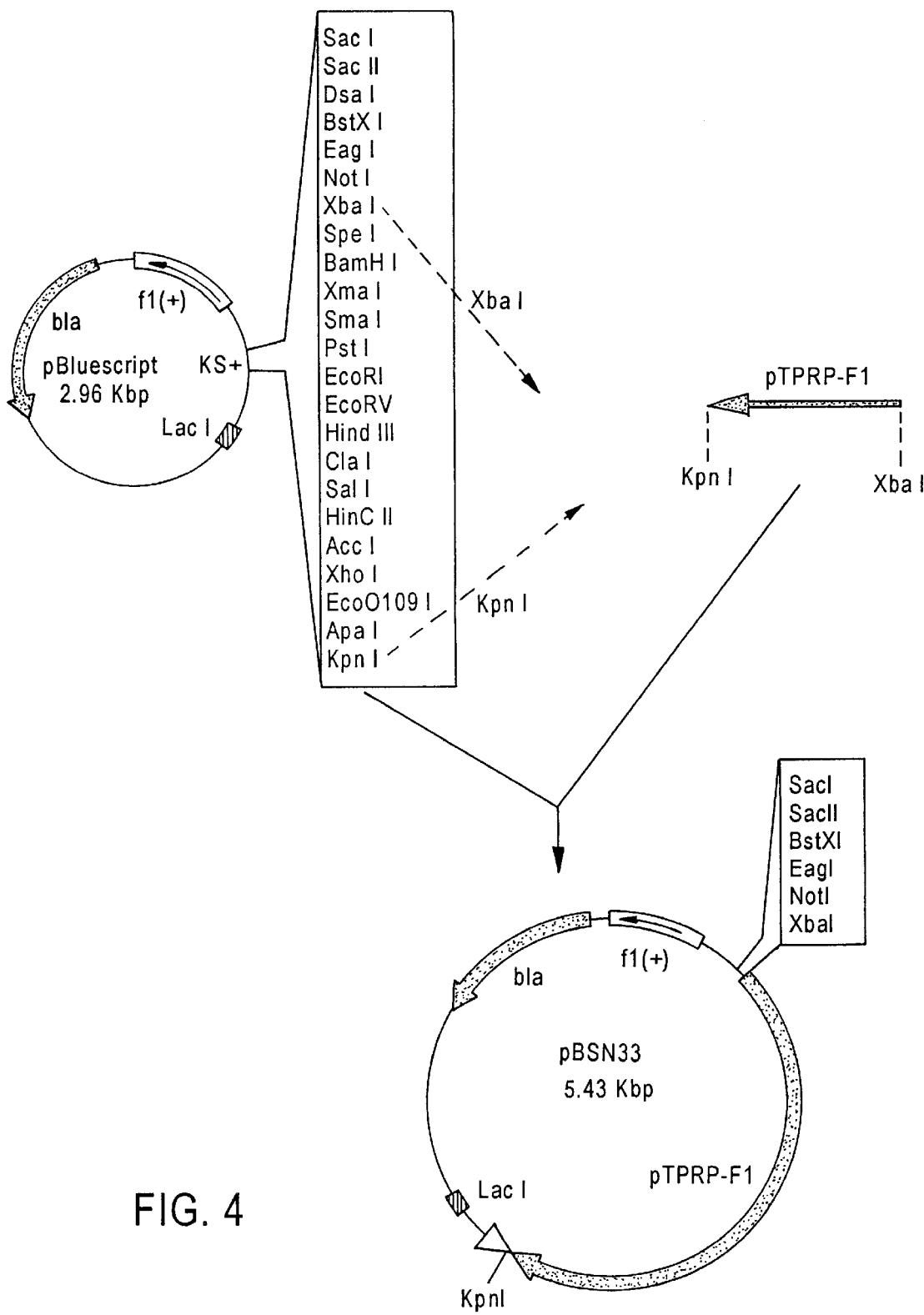
FIG. 4 is a diagram of the construction of plasmid pPSN33; The mutated pTPRP-F1 fragment was inserted into the Xba I and Kpn I sites of pBluescript KS+.

To ensure that the rolB gene will be translated from its native translation initiation codon, the translation initiation codon included in plasmid pBSN28, was abolished by in vitro mutagenesis: A PCR fragment containing the promoter with mutated initiation codon was prepared using the pBSN28 clone as a template, the sequence of the T7 promoter served as one primer (3' to 5') and the second primer was the following:

5' TGGTACCGGGCAATGAACAAAGTTCCA 3' (SEQ ID NO: 6). The bold letters designate the mutated sequence creating a new KpnI site at the 3' end of the promoter sequence. The PCR product was digested with KpnI and XbaI and ligated to pBluescript creating the plasmid pBSN33 (FIG. 4).

Figure 5:
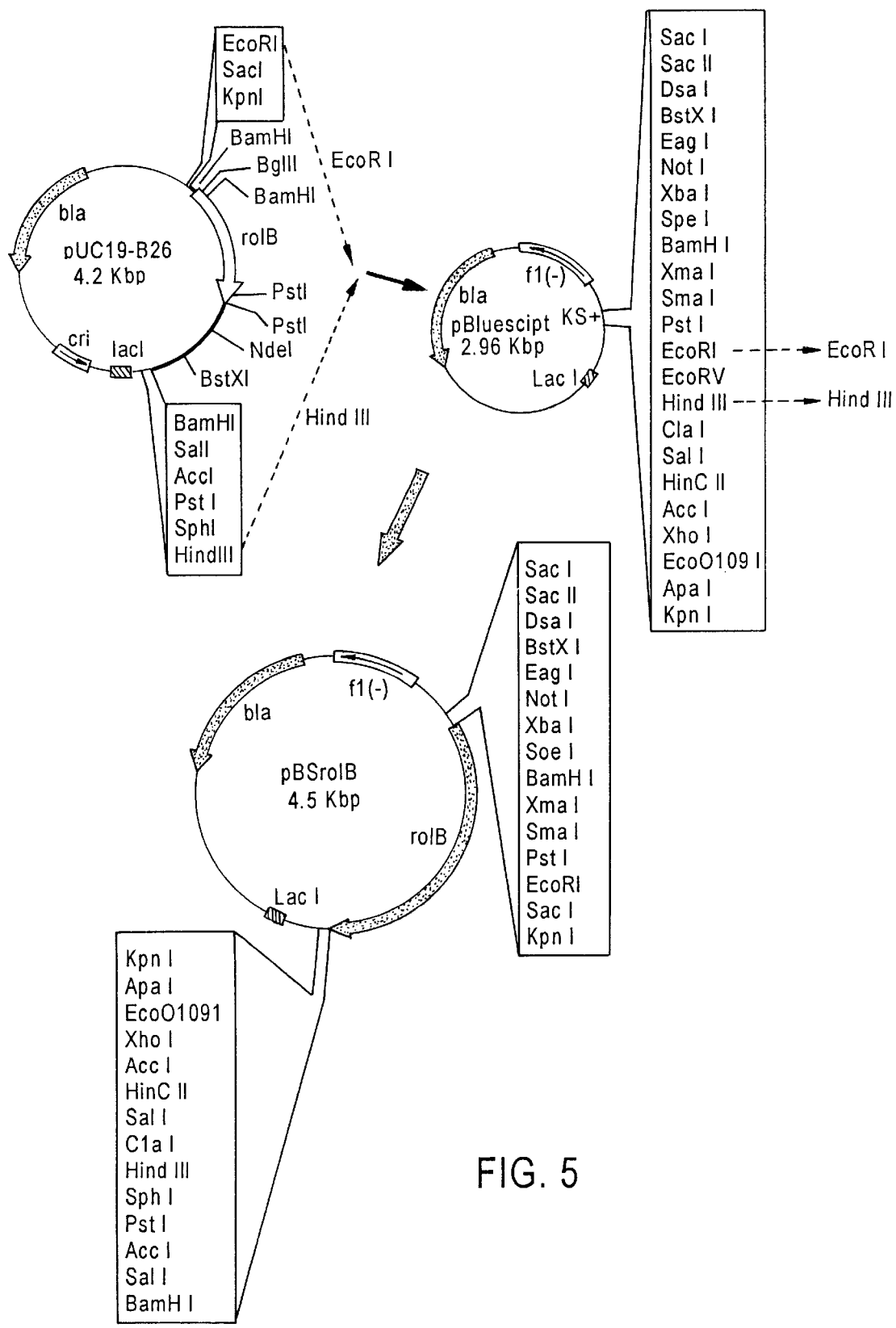
FIG. 5 is a diagram of the construction of plasmid pBSrolB; The EcoRI-HindIII fragment of pUC19-B26 was ligated into the corresponding sites of pBluescript KS+.

Construction of the plasmid pBSNrolB pUC19-B26 (supplied by J.Schell) harbors the sequence between nucleotides 9814 and 11324 according to Slighton et al. (Slighton J L, Durand-Tardif M, Jouanin L, Tepfer D (1986) Nucleotide sequence analysis of TL-DNA of *Agrobacterium rhizogenes* Agropine type plasmid. Identification of open reading frames. J Biol Chem 261:108–121). The sequence of rolB included in this plasmid is given in Table 5. The EcoRI-HindIII fragment of this plasmid was isolated and cloned into the EcoRI/HindIII-restriction cleavage sites of the plasmid pBluescript to form pBSrolB (FIG. 5).

Figure 6:
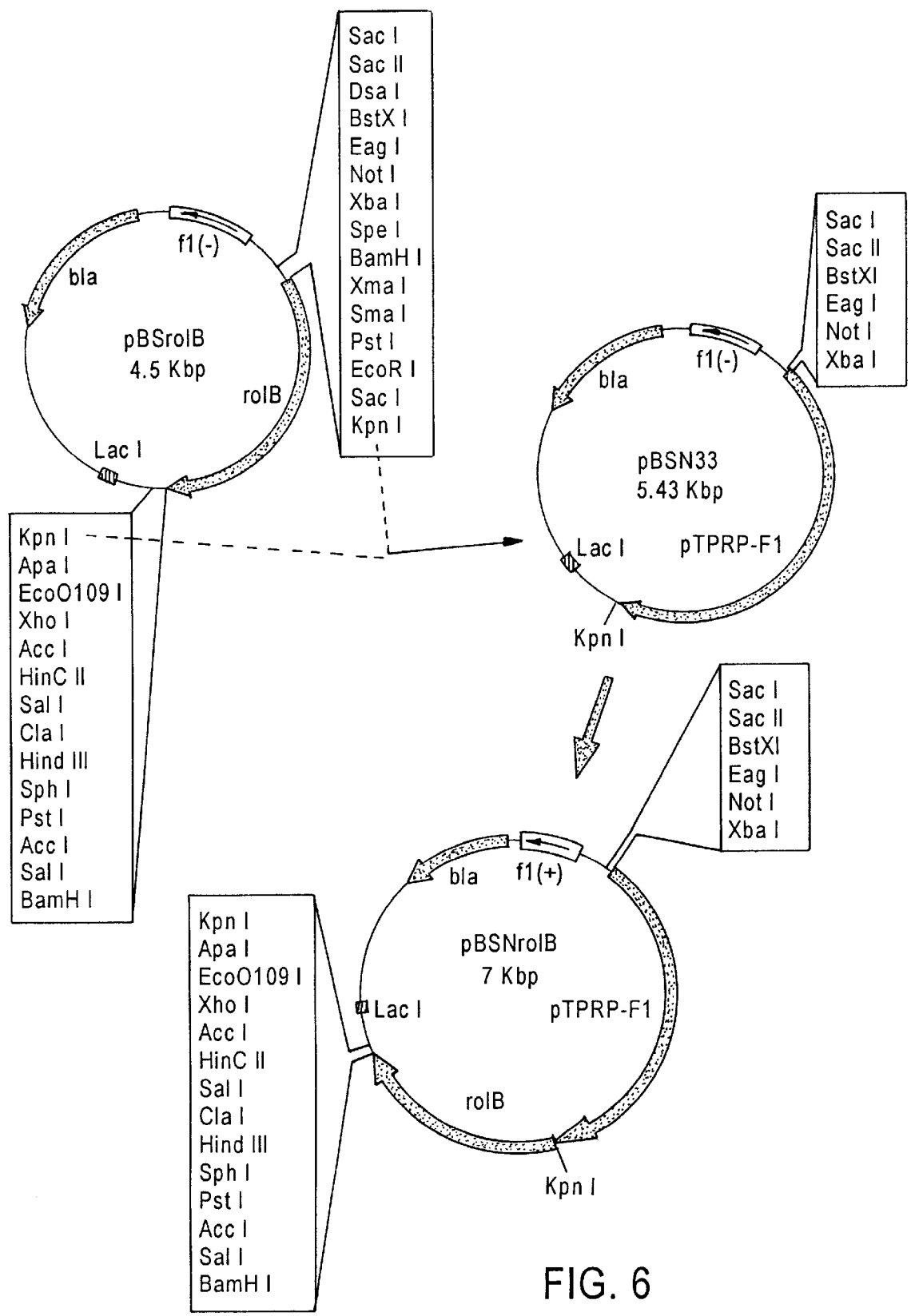
FIG. 6 is a diagram of the construction of plasmid pBSNrolB; The Kpn I fragment of pBSrolB was ligated into the Kpn I site of pBSN33.

The KpnI fragment of pBSrolB was isolated and subcloned into the KpnI site of pBSN33, and a clone with the rolB gene inserted in the correct orientation was identified by restriction enzyme analysis. This plasmid was named pBSNrolB (FIG. 6).

Construction of the binary plasmid pGB18rolB

Figure 7:
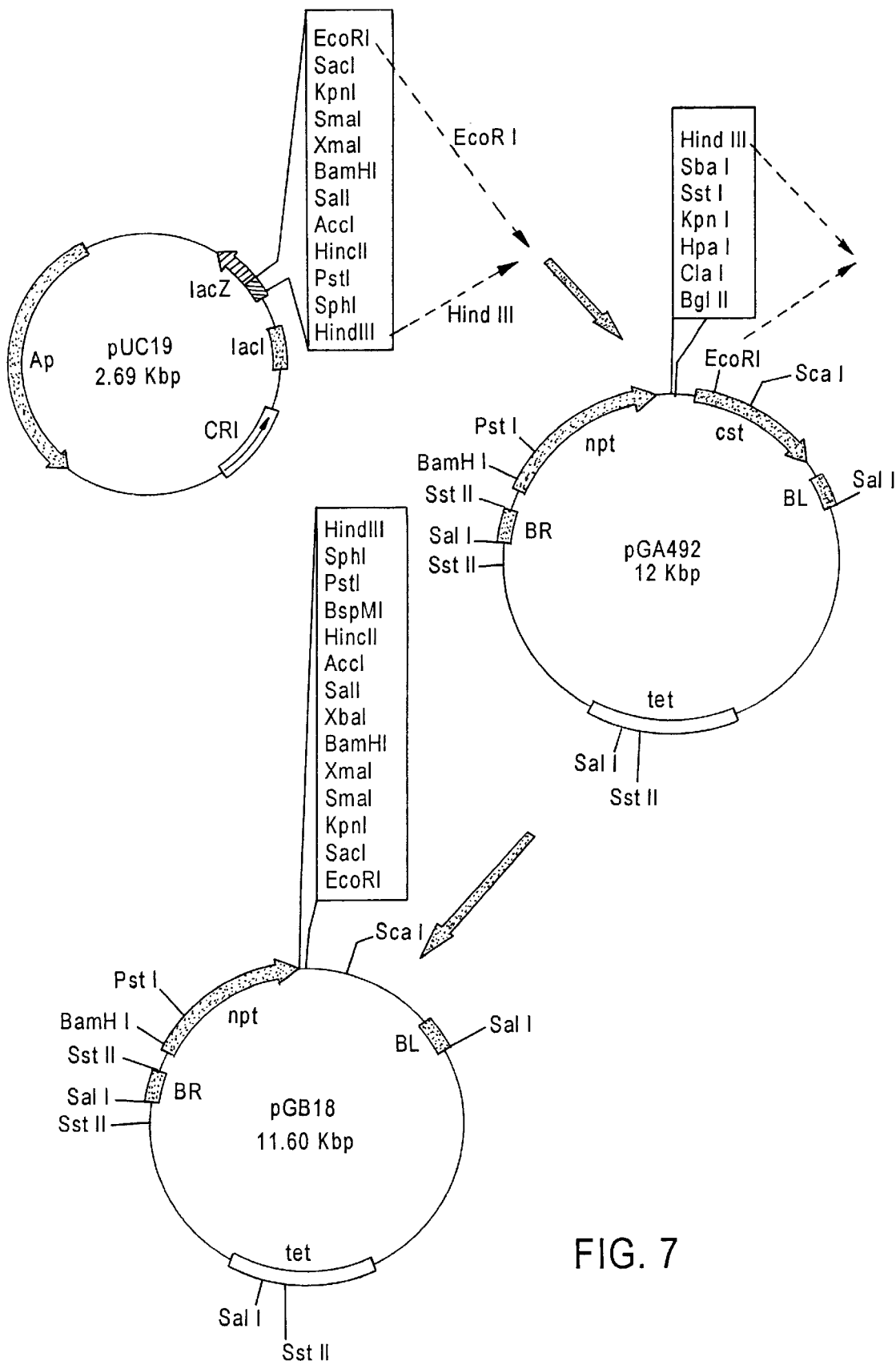
FIG. 7 is a diagram of the construction of plasmid pGB18; The multiple cloning site of pGA492 was replaced by the one of pUC19.
Figure 8:
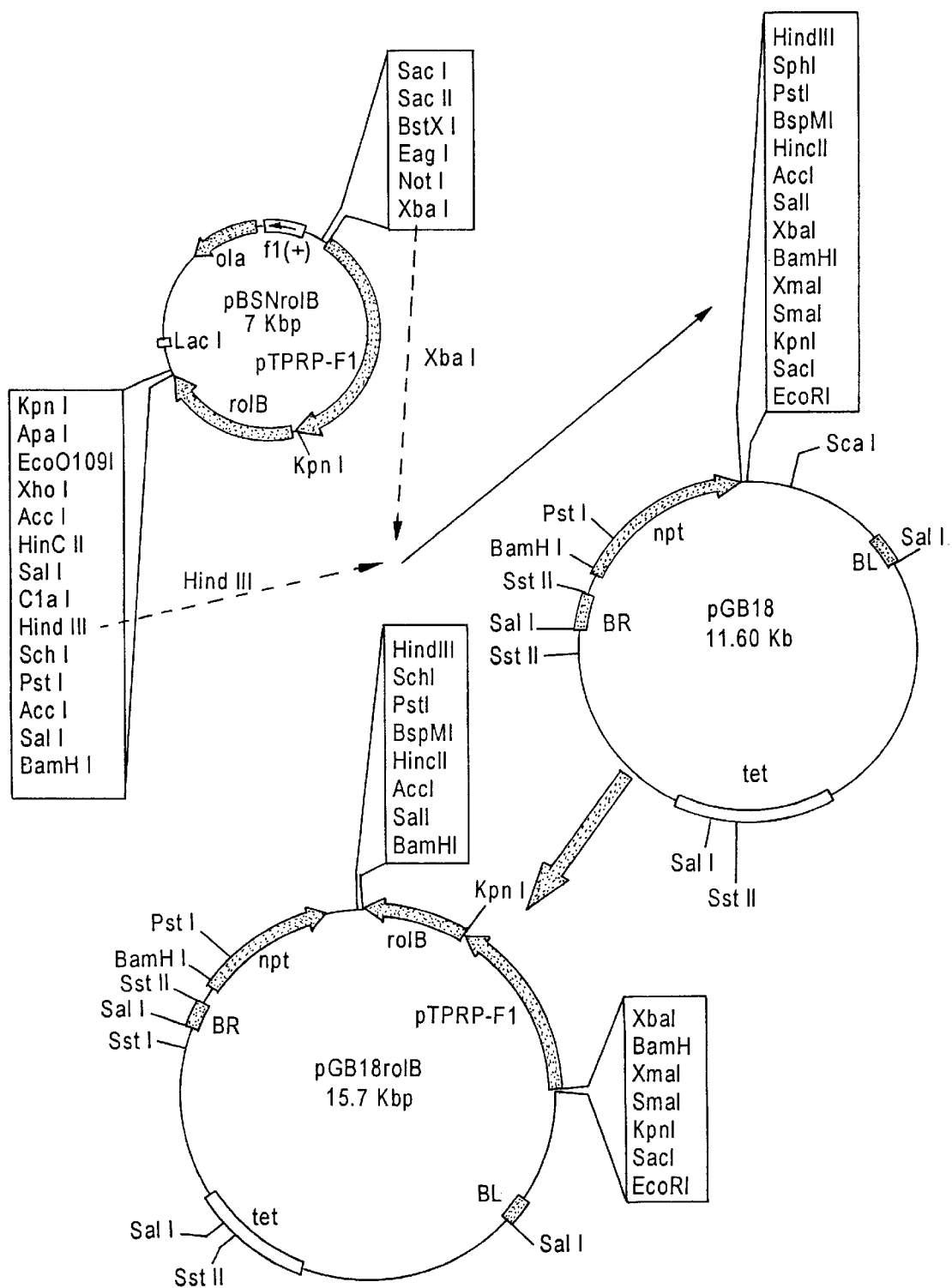
FIG. 8 is a diagram of the construction of plasmid pGB18rolB; The Xba-HindIII fragment of pBSNrolB was ligated into the corresponding sites of pGB 18.

The EcoRI-HindIII polylinker of plasmid pUC18 was isolated and subcloned into the EcoRI/HindIII-restriction cleavage sites of the plasmid pGA492 (An G 1986) Development of plant promoter expression vectors and their use for analysis of differential activity of nopaline synthase promoter in transformed tobaco cells Plant Physiol. 81:86–91) to form plasmid pGB18 (FIG. 7). The XbaI-BamHI fragment of pBSNrolB was isolated and subcloned into the XbaI/BamHI restriction cleavage sites of plasmid pGB18 to form plasmid pGB18rolB (FIG. 8).

Induction of Parthenocarpy in tomato via specific expression of the TPRP-F1::rolB Gene in the ovary.

Plant transformation

The binary vector pGB18rolB was transformed into the indeterminate tomato breeding line MP-1 by co-cultivation of cotyledons derived from 10-day-old seedlings with *Agrobacterium tumefaciens* strain EAH105 (Hood E E, Gelvin S B, Melchers L S, Hoekema A (1993) New Agrobacterium helper plasmids for gene transfer to plants. Trangenic Res. 2:208–218). Essentially, the protocol described by McCormick (McCormick S (1991) Transformation of tomato with *Agrobacterium tumefaciens* In: Plant tissue culture manual (Ed. K. Lindsey) B6: 1–9) was followed, except that the 'overnight' bacteria culture was resuspended in liquid MS (Murashige and Skoog 1962) A revised medium for rapid growth and bioassay with tobacco tissue cultures. Physiol Plant 15:473–496) medium before pouring over the cotyledons, and using 0.5 mg/L cefotaxime instead of carbenicillin. The cotyledons and the plantlets regenerated from them were propagated in the presence of 100 mg/L of kanamycin until rooted. Regenerated plants were planted in peat pellets (Jiffy-7, a/s Jiffy Products, Norway) for hardening (for 1–2 weeks) and then transferred to insect-proof greenhouse or net-house.

To select for transformed progenies, sterile seeds were germinated on selective medium (½ MS medium, 3% sucrose and 100 mg/L Kanamycin), where only transgenic seedlings develop a branched root system.

Description of the transgenic plants

Of the transgenic plants regenerated from breeding line MP-1, three were parthenocarpic primary (Ro) transgenic plants: MPB-4, MPB-12 and MPB-13, Transformation of the Ro plants was confirmed by PCR analysis, using primers for the selectable marker gene nptII, and by Southern analysis, using a KpnI fragment of the rolB gene as a probe.

The Southern analysis indicated that the MPB-4 Ro plant contains at least four inserts of the chimeric genes whereas both MPB-12 and MPB-13 contain two copies in tandem. The tandem pattern of insertion was confinmed by Southern analysis of $R_1$ and $R_2$ progenies of both MPB-12 and MPB-13.

Phenotypes of Ro Plants

Some phenotypic characteristics of the three Ro plants are summarized in Table 6.

1. Vegetative growth habit of Ro plants: Upon transplanting the Ro plants into pots, they developed a vegetative growth habit which did not differ significantly from that of the parental cultivar MP-1.

2. Reproductive development of the Ro plants: All the Ro plants developed multiple flowers. The flowers of plant MPB-4 manifested a typical 'parthenocarpic' mode of development: namely, the ovaries started to enlarge very early relatively to the flower's development when the petals were still completely closed, and the petals did not wilt and remained attached to the base of the developing fruit until torn away by the growing fruit. The MPB-4 pollen was not viable according to vital staining with fluorescein diacetate (Widholm J M (1972) The use of fluorescein diacetate and phenosafranine for determining viability of cultured plant cells. Stain Technol 17:1890194) and pollen germination test (Brewbaker J L & Kwack B H (1963) The essential role of calcium ion in pollen germination and pollen tube growth Amer J. Bot 50:859–865).

The flowers of MPB-13-Ro plant manifested a moderate mode of parthenocarpic-like development (early enlargement of the ovary and postponed wilting of the petals), the pollen was viable. The flowers of MPB-12-$R_0$ manifested even a milder parthenocarpic phenotype; their ovaries were slightly enlarged and wilting of the petals was postponed. Their pollen was viable.

3. Seedlessness and fruit characteristics of Ro plants: As summarized in Table 6, seedlessness was absolute in plant MPB-4, and in most of its fruits the columella was considerably larger than in the parental cultivar or in fruits of non-parthenocarpic transgenic plants. The locular cavities were full of jelly in most of the MPB-4 fruits, just in few the jelly fill was incomplete. Most of the fruits contained 4–5 locules whereas under the same growth conditions the MP-1 fruits usually consisted of 3–4 locules. Seeded fruits were not obtained from MPB-4 even following hand-pollination of very young flower buds with pollen of the parental line MP-1. This female sterility is apparently due to rapid enlargement of the ovary at very early stage of flower bud development, leading to closure or detachment of the style tube which prevents fertilization. Thus, plant PMB-4 is considered an obligate parthenocarpic one. This indeterminate plant is maintained by propagation from cuttings.

Plants MPB-12 and MPB-13 behaved as facultative parthenocarpic ones. Their seedless fruits were fill of jelly and contained 4 locules or more. In most MPB-13 fruits and in some of the MPB-12 fruits the columella was somewhat greater than in the parental line fruits. In some of the MPB-13 fruits the jelly was of greenish hue, especially in fruits developed at high temperatures. This phenomenon was also reported for auxin-induced fruits. (Abad & Monteiro 1989). The fasciation typical to auxin-induced parthenocarpic fruits was not observed in the seedless fruits of MPB-12 and MPB-13.

Among the seedless fruits of MPB-12-Ro developed in the summer, under extremely high temperatures, there was a tendency for a typical malformation; the fruits were oval rather than round, slightly flattened, and occasionally constricted in transverse section (a "peanut-like" appearance).

Phenotypes of R1 plants

1. Vegetative growth habit of R1 plants: Most of the $Kan^r$ seedlings of PMB-12-$R_1$ and all of the $Kan^r$ MPB-13-$R_1$ plants were characterized by broad cotyledons which rolled downwards. The severity of the phenomenon varied among the various plants. The root system of some of the MPB-13-$R_1$ seedlings was more developed than that of the control plants. The developed plants did not manifest auxin related malformations (such as leaf epinasty, stem curling or adventitious root development.

2. Reproductive development of the R1 plants: Flowers of the various $Kan^r$ MPB-12-$R_1$ plants were of normal appearance and mode of development, except for the lack of wilting of the petals which remained attached, to the base of the developing fruits, similar to the phenotype of the MPB-12-$R_0$ flowers. Flowers of the $Kan^r$ MPB-13-$R_1$ plants manifested varying degree of 'parthenocarpic' development (early enlargement of the ovary and postponed wilting of the petals), and the pollen was viable.

3. Seedlessness and fruit characteristics in R1 plants: As specified in Table 6, most of the fruits developed on the various $Kan^r$ MPB-12-R1 plants were seedless and full of jelly. Occasionally seeded fruits developed, most of them contained significantly less seeds than the parental cultivar, and the average weight and size of the seeds was significantly higher than that of the MP-1 fruits. The frequency of seeded fruits varied among the various $R_1$ plants. The fruits were not puffy; some of the fruits were of slightly flattened oval shape. Transverse constriction was not observed, apparently because the fruits did not develop under exceptionally high temperatures. Most of the fruits of the various MPB-13-$R_1$ plants were of regular shape, seedless, and full of jelly. Few seeded fruits developed, and most of their contained less seeds than MP-1.

Phenotypes of $R_2$ plants

1. Vegetative growth habit of R2 plants: The phenomenon of broad cotyledons was also observed in the $kan^r$ $R_2$ seedlings of MPB-12 and MPB-13. The developing plants were of normal growth habit.

2. Seedlessness and fruit characteristics in R2 plants: The fruits developed on $R_2$ progenies of MPB-12 and MPB-13 transformants were tested for several fruit indexes. These plants grew under pollination-permissive environmental conditions. Data analysis was based on information collected from two or three plants of the $R_2$ generation (Table 7), since no significant differences were found among the various $R_2$ plants derived from a common $R_1$ plant.

The transgenic fruits did not differ significantly (P<0.05) from the control fruits with regard to the average fruit weight, number of locules per fruit, or Brix value. However, even though pollination in the transgeneic plants was supported by vibrating the flowers, the fruits of all the transgenic plants had significantly (P<0.001) fewer seeds than those of the control plants. The seed number varied from zero up to 30–50 per fruit, among the various fruits developed on the same transgenic plant, reflecting the facultative nature of the parthenocarpy in these transgenic plants (Table 7).

In the parental line MP-1 there was a significant positive correlation between seed number and fruit weight ($r^2=0.386$, P=0.023, n=14). However, the highly significant decrease of seed number in the transgenic plants was not accompanied by a decease of fruit weight. Regression of fruit weight vs. seed number was insignificant for MPB-12.5-$R_2$ (n=23) $r^2=0.0279$, P=0.446, for MPB-13.3-R2 (n=15), $r^2=0.0086$, P=0.7419, and for MPB-13.4-R2 (n=7), $r^2=0.1115$, P=0.4642. This fact indicates that the expression of the transgene completely compensates for the seed contribution to fruit weight.

All the seedless fruits were full of jelly. The color of jelly of the transgenic fruits was not always as red as that of the control; in many of the fruits it was more of yellow-orange color with traces of green hue.

It will be appreciated by persons skilled in the art that the present invention is not limited to what has been particularly shown and described herein above. Rather the scope of the present invention is defined only by the claims which follow.

What is claimed is:

1. A method for the production of genetic parthenocarpy in plants comprising the steps of:
   A. providing a cassette including:
      i. a DNA sequence coding for a protein comprising the sequences of the rolB gene that modulates the auxin effects in plants; and
      ii. a promoter specific for the ovary between anthesis and early fruit development to control the DNA sequence; and
   B. introducing the cassette into a plant comprising the steps of:
      i. transforming plant material, comprising seed derived from cotyledons, by steps comprising:
         a. providing a plasmid incorporating said cassette;
         b. introducing said plasmid into *A. tumefaciens*; and
         c. incorporating said plasmid into the plant material by co-cultivation with the *A. tumefaciens* including the plasmid; and
      ii. regenerating transformed plants: and
   C. screening said plant for either facultative or obligatory parthenocarpic characteristics.

2. A method according to claim 1 wherein the promoter specific for the ovary between anthesis and early fruit development includes the sequences as specified in SEQ ID NO: 1.

3. A method according to claim 1 wherein the promoter specific for the ovary between anthesis and early fruit development includes the sequences as specified in SEQ ID NO: 2.

4. A method according to claim 1 wherein the promoter specific for the ovary between anthesis and early fruit development includes the sequences as specified in SEQ ID NO:3.

5. A method according to claim 1 wherein the promoter specific for the ovary between anthesis and early fruit development includes the sequences as specified in SEQ ID NO: 4.

6. A method according to claim 1 wherein the step of screening includes:
   growing the plant to produce fruit; and
   examining the fruit for seed production under at least one condition selected from the group consisting of: fertilization permissive conditions and fertilization restrictive conditions.

7. A method according to claim 1 wherein the plant is a tomato plant.

8. A tomato plant produced by the method of claim 1.

9. Fruit of a tomato plant produced by the method of claim 1.

* * * * *

SEQUENCE LISTING

<160> NUMBER OF SEQ ID NOS: 6

<210> SEQ ID NO 1
<211> LENGTH: 12839
<212> TYPE: DNA
<213> ORGANISM: TPRP-F1 GENOMIC CLONE
<220> FEATURE:
<221> NAME/KEY: unsure
<222> LOCATION: (5)..(11322)
<223> OTHER INFORMATION: "n"'s are any nucleic residue

<400> SEQUENCE: 1

```
absuncthtr gnmccnncud ngbthrmtrr gnthsuncth rmtrrgntnd ngrmwasntu      60
bshdarrths unctndngrm wasubshdar rthatgcdnr ntdnbdttrs stnsthtran     120
satnntatnc dnusdrthgu srmtrrssna nayssthund rndbdgstns thtranscrt    180
nntatnstun ubshddataa tgcatcccaa ataggcgagt gagatggaag ggaggcaatg    240
acacgaaatt tgtctatgtg tcctagatat gtaagaattc actgatatat tgagtgtatc    300
tagaataaat taacttgatt ttgagtccat gtatttagag atacatgtat ctggacatat    360
caaagtctga taaaattcat aatattaaaa catagagtgt ctttaagtaa ttagctcata    420
cactagaatg atttttgtaa gttacactta aataaattgt tttggcccat gagccaactg    480
accccaatca agcctcaagg gcttatatga atcgagttta taagccctag tttcaaatga    540
gcttgaaaaa ttctatctca actatatcca aataatagat tggattggat cgaatcccat    600
gggctacgca ttttgatagc tctagttgta accctaacta atgatgaaaa tattttgac     660 atgatattta ttttattacc acaattattt taatatttat tttatacata atatatttct    720
tataaaatta ctacacataa ttgtctgatg actgtagaag agtagttgac aaaatattat    780
cgcaatgtca ttgttattat aggtacaaat tattaagtga aagtagaata taacgtgaaa    840
tcgaattaaa aaaataatca gattgtaatg aaatattatt agagagaagt attaaagtac    900
ctataaactt ggcacaaatt attagttta tttctgtact attgacaacc ttaaaaacta     960
cttgactaac taaacttaga tacacctaat tttttgtagg agcatgaaac tcttaatgaa   1020
tggccaagag aagtgttgaa agcaccccca aacttgatga gaatttagag tgtatttcac    1080
ccatattgca agattgtaag tgtatttaaa tttagttaat caattaaata aatgtatttt    1140
gaattccaat aattcaagga tgaaacaaat agttcatatt gaatttaaat gttttttgaa    1200
tacttctttt tttctcaata ttgactaact agtacaacca ggtttgatta tgatttagat    1260
ttgtaccaca taagattatt aaagagaaaa acattctttg atgattcatc ttttaaattc    1320
```

-continued

```
tcaaagctcg aatacgtaaa atctaattaa tatcagcata atctcattca gaggcggagc    1380
tagccttgtg ttaggggta ttcaaacctt ctttgactga aaattttatt atttatacat     1440
```

```
tcaaagctcg aatacgtaaa atctaattaa tatcagcata atctcattca gaggcggagc    1380
tagccttgtg ttaggggta ttcaaacctt ctttgactga aaattttatt atttatacat     1440
gtttaaaatt acttttaat gtatatataa tagatatcaa attctttaat ttgtatttaa     1500
ttctataaat attaaattac tttattaaaa attctaattc tgtcactcgt tcatttcatc    1560
acattcttga cggtgatggt agtgataatt acattgattg gagccacatg ggccgctact    1620
ttttaaaaag gatgaaacct tggaatgtag tgaatgttga gtctcaatag ctcaatcacg    1680
gactcaacag caaaggtaag tgccaaaaat ctgtcctctt tttcccttct ccaattggag    1740
atactgtcac cttggacaaa taatatttga aaattttggc ctaaaagtta ggtttggagc    1800
cgtatggtaa tttgataaca caaattatta tataattgat atatcaagta tatatatcca    1860
aagttgtcgc attcttcgtt tcaatttgtt tctctcacta aaattttcaa ttcactttt     1920
aaaaaatcga taaattttta ataactttt acataacata ttcaaaatta caaaataaa      1980
ggatatttt atatgtttat tttaatgta agattaaata tttagaattc ttttaagaa       2040
cggtacaagc aaattaaaag agagaaggta tattagtggg cctatgtatc tttgtataca    2100
tatgcctctc aaagagctac ctgatgagtc tatatatctt tgttgatagt gatttaacaa    2160
tttatgtatg tacgtactaa gacatgttaa ataagtacct agagaaagat ttttggaaaa    2220
gtgaaaacag caataaagaa aagtcattta aacactttcc aacaaacatt tggtaatcga    2280
ttttaattac ccacttaaac aaaactattt gtacgtaaaa tgtttaagta gaaaagagat    2340
ttttttttaa aaaaaaaga aggcaagagg tcatatatct gaccttcct taaatccccg      2400
cgtataacac tttctttttt tttgtgtgtg tatgttcagg aacatttata ttttctattt    2460
gaaatttctc attaagtcaa attcgaaatc ttttaaataa tgtagaaaaa tctcattata    2520
tttaacaatc ccacttgatg aattcctaaa cattttctat aaaataacac taaatcttta    2580
attatacata ttcataacct aactcaagca tcttgtcggt aaaaatcatt agaaaagaat    2640
tggaaatagg gaaattcata gacatatttt ggttagtatc tttgtctata agaatgggtg    2700
tgttaaagag ctagtgccat agtgtaccat tctattggta gcatttggca agagttattc    2760
cctctctcca taccaatgga gaagtttaat cttgctagag tcttattgtt gcttcttcaa    2820
cttggaactt tgttcattgc ccatgcatgt ccttattgca tgtccttatt gtccatatcc    2880
tccttccacc ccaaaacacc caaaattgcc tcctaaggtg aaaccaccct ctacacaacc    2940
tccacatgtg aaaccaccttt ctaccctaa acaccctaaa gatcctccac atgtgaagcc   3000
accttctacc cctaaacaac caccatatgt gaaaccaccct actacccta aacaccctcc   3060
acatgttaaa ccaccttcca cccctaaaca ccctaaacac cccccacaaa aaccatgccc    3120
tcctccatct catcatggtc ctaagccacc aattgtaaaa cctccacatg taccaagacc    3180
tcctatagtg catcctcctc ccattgtctc tccaccttcc acacctaaac caccaaaaac    3240
accaccattc actccaaaac caccatcacc aataccacct attgtttcac ccctattgt    3300
ttatccacca atcactccaa caccacctat tgtccatcca ccagtcactc caaaaccacc    3360
atcaccaaca cctcctattg tttcaccccc cattgtttat ccaccaatca ctccaacacc    3420
acctgttgtg tcacctccaa tcattccaac accacctatt gtctctccac cttttgtccc    3480
caatcctccc gtggtaatac caccaccta cgtgccaagt cctccggttg ttactccacc    3540
catagttcca acacccccta caccatgccc accaccacca ccaccaccag caataatacc    3600
atcaccacca gcacaaccaa cttgccccat tgatgctctc aagctaggtg cttgtgtgga    3660
```

```
cgtgttagga ggactaatcc acattggaat cggtggaagt gctaagcaaa catgttgtcc    3720
acttctagga ggactagtag acttggatgc agccatttgt ctttgcacaa ctattagact    3780
caagctctta aacataaaca tcattcttcc cattgctcta caggttctta ttgatgattg    3840
tggcaagtat ccacccaaag acttcaagtg tccttcaacc taaatcaagg tttccacttt    3900
ttctcacttt caattattac tcactcctac tcaatttatg tggtacagtt gacatttcaa    3960
gtattaggcc caattttctt agctcggaat tttttaaat ctctttaaat attttgattt    4020
atactactta ttacgtagtt ttcataagta taaatttcat ttcatatatg aattcacggt    4080
caaaaattta agtttatttt aaccaatgcc acataactta gaacatacaa atatctttt    4140 gatcaagatt tggcaattcg tatacaataa tctttagcaa gtaatatgta taccaacatt    4200
atgtaatatg atgcagcata ttaaacagga catttgactg atactgccgc attgtcatag    4260
ttgaaggcac aataaatgtg tgaaagttca atttccattt tatcatggca ataaattgag    4320
aaaacaaagg agggatatta attaagcttt aatttggcgt gtttaattag cttttgatta    4380
atgtactgaa tgttgtattt acattattgt tttagggaaa tactaatggt atttagtata    4440
gtggagtatg aatgctgatt tgattgtatg aacacgaatg aatgaggaaa gaatcaccta    4500
atttatcacg tgttaatctt abthsuncth trrmtrncud dnthbnarya smdgbrbgth    4560
sunccrrsnd stntabstnc tagaataaat taacttgatt ttgagtccat gtatttagag    4620
atacatgtat ctggacatat caaagtctga taaaattcat aatattaaaa catagagtgt    4680
ctttaagtaa ttagctcata cactagaatg atttttgtaa gttacactta aataaattgt    4740
tttggcccat gagccaactg accccaatca agcctcaagg gcttatatga atcgagttta    4800
taagccctag tttcaaatga gcttgaaaaa ttctatctca actatatcca aataatagat    4860
tggattggat cgaatcccat gggctacgca ttttgatagc tctagttgta accctaacta    4920
atgatgaaaa tattttttgac atgatattta ttttattacc acaattattt taatatttat    4980
tttatacata atatatttct tataaaatta ctacacataa ttgtctgatg actgtagaag    5040
agtagttgac aaaatattat cgcaatgtca ttgttattat aggtacaaat tattaagtga    5100
aagtagaata taacgtgaaa tcgaattaaa aaaataatca gattgtaatg aaatattatt    5160
agagagaagt attaaagtac ctataaactt ggcacaaatt attagttta tttctgtact    5220 attgacaacc ttaaaaacta cttgactaac taaacttaga tacacctaat tttttgtagg    5280
agcatgaaac tcttaatgaa tggccaagag aagtgttgaa agcacccca aacttgatga    5340 gaatttagag tgtatttcac ccatattgca agattgtaag tgtatttaaa tttagttaat    5400
caattaaata aatgtatttt gaattccaat aattcaagga tgaaacaaat agttcatatt    5460
gaatttaaat gttttttgaa tacttctttt tttctcaata ttgactaact agtacaacca    5520
ggtttgatta tgatttagat ttgtaccaca taagattatt aaagagaaaa acattctttg    5580
atgattcatc ttttaaattc tcaaagctcg aatacgtaaa atctaattaa tatcagcata    5640
atctcattca gaggcggagc tagccttgtg ttagggggta ttcaaacctt ctttgactga    5700
aaattttatt atttatacat gtttaaaatt actttttaat gtatatataa tagatatcaa    5760
attctttaat ttgtatttaa ttctataaat attaaattac tttattaaaa attctaattc    5820
tgtcactcgt tcatttcatc acattcttga cggtgatggt agtgataatt acattgattg    5880
gagccacatg ggccgctact ttttaaaaag gatgaaacct tggaatgtag tgaatgttga    5940
gtctcaatag ctcaatcacg gactcaacag caaaggtaag tgccaaaaat ctgtcctctt    6000
tttcccttct ccaattggag atactgtcac cttggacaaa taatatttga aaattttggc    6060
```

-continued

```
ctaaaagtta ggtttggagc cgtatggtaa tttgataaca caaattatta tataattgat      6120
atatcaagta tatatatcca aagttgtcgc attcttcgtt tcaatttgtt tctctcacta      6180
aaattttcaa ttcactttt  aaaaaatcga taaatttta  atataacttt  acataacata     6240
ttcaaaatta caaaaataaa ggatatttt  atatgtttat ttttaatgta agattaaata      6300
tttagaattc ttttaagaa  cggtacaagc aaattaaaag agagaaggta tattagtggg      6360
cctatgtatc tttgtataca tatgcctctc aaagagctac ctgatgagtc tatatatctt      6420
tgttgatagt gatttaacaa tttatgtatg tacgtactaa gacatgttaa ataagtacct      6480
agagaaagat ttttggaaaa gtgaaaacag caataaagaa aagtcattta aacactttcc      6540
aacaaacatt tggtaatcga ttttaattac ccacttaaac aaaactattt gtacgtaaaa      6600
tgtttaagta gaaagagat  ttttttttaa aaaaaaaga  aggcaagagg tcatatatct      6660
gacccttcct taaatccccg cgtataacac tttcttttt  tttgtgtgtg tatgttcagg      6720
aacatttata ttttctattt gaaatttctc attaagtcaa attcgaaatc ttttaaataa      6780
tgtagaaaaa tctcattata tttaacaatc ccacttgatg aattcctaaa catttctat      6840 aaataacac  taaatcttta attatacata ttacatacct aactcaagca tcttgtcggt      6900
aaaaatcatt agaaaagaat tggaaatagg gaaattcata gacatatttt ggttagtatc      6960
tttgtctata agaatgggtg tgttaaagag ctagtgccat agtgtaccat tctattggta      7020
gcatttggca agagttattc cctctctcca taccaatgga gaagtttaat cttgctagag      7080
tcttattgtt gcttcttcaa cttggaactt tgttcattgc cctabashrt rrmtrthatc      7140
nrsvaryand mbryscctyr mntabstnaa ttccaataat tcaaggatga aacaaatagt      7200
tcatattgaa tttaaatgtt ttttgaatac ttcttttt  ctcaatattg actaactagt      7260
acaaccaggt ttgattatga tttagatttg taccacataa gattattaaa gagaaaaaca      7320
ttctttgatg attcatcttt taaattctca aagctcgaat acgtaaaatc taattaatat      7380
cagcataatc tcattcagag gcggagctag ccttgtgtta gggggtattc aaaccttctt      7440
tgactgaaaa ttttattatt tatacatgtt taaaattact ttttaatgta tatataatag      7500
atatcaaatt cttaatttg  tatttaattc tataaatatt aaattacttt attaaaaatt      7560
ctaattctgt cactcgttca tttcatcaca ttcttgacgg tgatggtagt gataattaca      7620
ttgattggag ccacatgggc cgctactttt taaaaaggat gaaaccttgg aatgtagtga      7680
atgttgagtc tcaatagctc aatcacggac tcaacagcaa aggtaagtgc caaaaatctg      7740
tcctcttttt cccttctcca attggagata ctgtcacctt ggacaaataa tatttgaaaa      7800
ttttggccta aaagttaggt ttggagccgt atggtaattt gataacacaa attattatat      7860
aattgatata tcaagtatat atatccaaag ttgtcgcatt cttcgtttca atttgtttct      7920
ctcactaaaa ttttcaattc actttttaaa aaatcgataa atttttaata aactttaca      7980 taacatattc aaaattacaa aaataaagga tatttttata tgtttatttt taatgtaaga      8040
ttaaatattt agaattcttt ttaagaacgg tacaagcaaa ttaaaagaga gaaggtatat      8100
tagtgggcct atgtatcttt gtatacatat gcctctcaaa gagctacctg atgagtctat      8160
atatctttgt tgatagtgat ttaacaattt atgtatgtac gtactaagac atgttaaata      8220
agtacctaga gaaagatttt tggaaaagtg aaaacagcaa taaagaaaag tcatttaaac      8280
actttccaac aaacatttgg taatcgattt taattaccca cttaaacaaa actatttgta      8340
cgtaaaatgt ttaagtagaa aagagatttt tttttaaaaa aaaagaaagg caagaggtca      8400
```

```
tatatctgac ccttccttaa atccccgcgt ataacactttt cttttttttt gtgtgtgtat    8460
gttcaggaac atttatattt tctatttgaa atttctcatt aagtcaaatt cgaaatcttt    8520
taaataatgt agaaaaatct cattatattt aacaatccca cttgatgaat tcctaaacat    8580
tttctataaa ataacactaa atctttaatt atacatatta catacctaac tcaagcatct    8640
tgtcggtaaa aatcattaga aaagaattgg aaatagggaa attcatagac atattttggt    8700
tagtatcttt gtctataaga atgggtgtgt taaagagcta gtgccatagt gtaccattct    8760
attggtagca tttggcaaga gttattccct ctctccatac caatggagaa gtttaatctt    8820
gctagagtct tattgttgct tcttcaactt ggaactttgt tcattgccct abanatrnat    8880
vcmbnatnsu ncrmthtrrm trthatcnrs varyanddvn gmbryscccty rmusdttaba    8940 tgcatcccaa ataggcgagt gagatggaag ggaggcaatg cacgaaatt tgtctatgtg     9000 tcctagatat gtaagaattc actgatatat tgagtgtatc tagaataaat taacttgatt    9060
ttgagtccat gtatttagag atacatgtat ctggacatat caaagtctga taaaattcat    9120
aatattaaaa catagagtgt ctttaagtaa ttagctcata cactagaatg attttttgtaa   9180 gttacactta aataaattgt tttggcccat gagccaactg accccaatca agcctcaagg    9240
gcttatatga atcgagtttta taagccctag tttcaaatga gcttgaaaaa ttctatctca   9300
actatatcca aataatagat tggattggat cgaatcccat gggctacgca ttttgatagc    9360
tctagttgta acccaacta atgatgaaaa tattttgac atgatattta ttttattacc      9420
acaattattt taatatttat tttatacata atatatttct tataaaatta ctacacataa    9480
ttgtctgatg actgtagaag agtagttgac aaaatattat cgcaatgtca ttgttattat    9540
aggtacaaat tattaagtga aagtagaata taacgtgaaa tcgaattaaa aaaataatca    9600
gattgtaatg aaatattatt agagagaagt attaaagtac ctataaactt ggcacaaatt    9660
attagtttta tttctgtact attgacaacc ttaaaaacta cttgactaac taaacttaga    9720
tacacctaat tttttgtagg agcatgaaac tcttaatgaa tggccaagag aagtgttgaa    9780 agcacccccca aacttgatga gaatttagag tgtatttcac ccatattgca agattgtaag    9840
tgtatttaaa tttagttaat caattaaata aatgtatttt gaattccaat aattcaagga    9900
tgaaacaaat agttcatatt gaatttaaat gttttttgaa tacttctttt tttctcaata    9960
ttgactaact agtacaacca ggtttgatta tgatttagat ttgtaccaca taagattatt   10020
aaagagaaaa acattctttg atgattcatc ttttaaattc tcaaagctcg aatacgtaaa   10080
atctaattaa tatcagcata atctcattca gaggcggagc tagccttgtg ttaggggta    10140 ttcaaacctt ctttgactga aaattttatt atttatacat gtttaaaatt acttttttaat  10200 gtatatataa tagatatcaa attctttaat ttgtatttaa ttctataaat attaaattac   10260
tttattaaaa attctaattc tgtcactcgt tcatttcatc acattcttga cggtgatggt   10320
agtgataatt acattgattg gagccacatg ggccgctact ttttaaaaag gatgaaacct   10380
tggaatgtag tgaatgttga gtctcaatag ctcaatcacg gactcaacag caaaggtaag   10440
tgccaaaaat ctgtcctctt tttccccttct ccaattggag atactgtcac cttggacaaa    10500
taatatttga aaattttggc ctaaaagtta ggtttggagc cgtatggtaa tttgataaca    10560
caaattatta tataattgat atatcaagta tatatatcca aagttgtcgc attcttcgtt    10620
tcaatttgtt tctctcacta aaattttcaa ttcacttttt aaaaaatcga ttttaattac   10680
ccacttaaac aaaactatt gtacgtaaaa tgtttaagta gaaagagat tttttttaa      10740 aaaaaaaga aggcaagagg tcatatatct gaccttcct taaatcccg cgtataacac       10800
```

```
tttctttttt tttgtgtgtg tatgttcagg aacatttata ttttctattt gaaatttctc    10860
attaagtcaa attcgaaatc ttttaaataa tgtagaaaaa tctcattata tttaacaatc    10920
ccacttgatg aattcctaaa cattttctat aaaataacac taaatcttta attatacata    10980
ttacatacct aactcaagca tcttgtcggt aaaaatcatt agaaaagaat tggaaatagg    11040
gaaattcata gacatatttt ggttagtatc tttgtctata agaatgggtg tgttaaagag    11100
ctagtgccat agtgtaccat tctattggta gcatttggca agagttattc cctctctcca    11160
taccaatgga gaagtttaat cttgctagag tcttattgtt gcttcttcaa cttggaactt    11220
tgttcattgc cctabthsun cthrbgnncu ddnthbnary vctrgbrbsg thsuncstha    11280
trsntdnsgh tmtathtran satnntatnc dnstnsrsnt dnbdttrsgg cacttgcctt    11340
tttcgtaact atccaactca catcacaatg gatcccaaat tgctattcct tccacgattt    11400
caaccagtag atctcactcc agcatggagc cagataaacc tattcgaggg gatccgattt    11460
gcttttgcaa tctatagccg tgactatagc aaacccctcc tgcatttcca gaacgatgg    11520 gctcttgcag tgctagattt gaaggaaaac tctccaccga tatatatact taaacaacta    11580
gctgagctct tgaagaacaa agtctgctat catcctccta tgtttgttag tcagccggat    11640
ctggctcgag aaaacgacca acatgtattt gtctatcttt ctcgcgagaa gatgcagaaa    11700
gtgctgaagg aacaatccat tacatttgga atggaggccg tgctggcgac aacgattcaa    11760
ccatatcgga gcgagctcgc cctccaggag atgctccgtg ttcacaacct tgcttggccg    11820
cacagccgca cggaggaacc tgatttagaa tgcttcatcg ccattttcgc aagttccttg    11880
ttcattcact tgctggagtt aaaagtgacc aacgtttacg ggagagaggt agcttgcacc    11940
ttctttctgc ggcgagggac tgaaaaccgc ccctatgatg ttgtagcttg cggcaccaca    12000
caattcacca aaaatgccct cgggatatca cgtccggccg cctcctcacc ggagccagac    12060
ctaaccctgc gactctcggg gcctgatcag gaaggcgagg agggcgtcat gaagcctgct    12120
gcagtaaacc tgaagaaaga agcctaaagc cgacttgaac tccccctgca ggcaaccttt    12180
atctataagt ttgtcataag ttctatgtac cctcccgcag tctgtgacac agaaccttgg    12240
gagttgtagc gtacgttgta atgtgttgac ctattttctt gtactaaata ttttcttctg    12300
tgttgatcct gctgctgaat tttgccaaaa acagcacatg ctcatgac tatctaatct    12360 actacacata tattgcagta tcaacaacaa cgacacacct ggacttataa tattatagtt    12420
caacagtaca tttgacataa aacattttca cgacattaca caaacgctct aaagagacgt    12480
taaagtacta tattaataaa acaggacaat cgcgccatgg ctcgcagctt attttaactt    12540
aacagaacat attcgatatc atctccggcg tggaaatgaa tcgaagaccg ccagccacgt    12600
gcgtattaat cccgtaggtt tgtttcgaaa tgcgtattaa tcccgtaggt ctgaattttc    12660
acgtccggcg acaaagggtc ccttcgcagc aactcgcggg tcgttgaacg tcccggtcgg    12720
gcttgggaag tcatggccaa aggagtggtg ctcagattgg ctggctcagc aagatggtcg    12780
cgttcgcccg gggatacccg tttggccttc ctcttggcct ttgcacgcct aacaagctt    12839
```

<210> SEQ ID NO 2
<211> LENGTH: 4518
<212> TYPE: DNA
<213> ORGANISM: TPRP-F1 PROMOTOR
<220> FEATURE:
<221> NAME/KEY: unsure
<222> LOCATION: (6)..(191)
<223> OTHER INFORMATION: "n"'s are any nucleic residue

<400> SEQUENCE: 2

```
tabsunctht rgnmccnncu dngbthrmtr rgnthsunct hrmtrrgntn dngrmwasnt      60
ubshdarrth sunctndngr mwasubshda rrthatgcdn rntdnbdttr sstnsthtra     120
nsatnntatn cdnusdrthg usrmtrrssn anayssthun drndbdgstn sthtranscr     180
tnntatnstu nubshddata atgcatccca aataggcgag tgagatggaa gggaggcaat     240
gacacgaaat ttgtctatgt gtcctagata tgtaagaatt cactgatata ttgagtgtat     300
ctagaataaa ttaacttgat tttgagtcca tgtatttaga gatacatgta tctggacata     360
tcaaagtctg ataaaattca taatattaaa acatagagtg tctttaagta attagctcat     420
acactagaat gatttttgta agttacactt aaataaattg ttttggccca tgagccaact     480
gaccccaatc aagcctcaag ggcttatatg aatcgagttt ataagccta gtttcaaatg      540
agcttgaaaa attctatctc aactatatcc aaataataga ttggattgga tcgaatccca     600
tgggctacgc attttgatag ctctagttgt aaccctaact atgatgaaaa tatttttgac     660
atgatattta ttttattacc acaattattt taatatttat tttatacata atatatttct     720
tataaaatta ctacacataa ttgtctgatg actgtagaag agtagttgac aaaatattat     780
cgcaatgtca ttgttattat aggtacaaat tattaagtga agtagaata taacgtgaaa      840
tcgaattaaa aaaataatca gattgtaatg aaatattatt agagagaagt attaaagtac     900
ctataaactt ggcacaaatt attagtttta tttctgtact attgacaacc ttaaaaacta     960
cttgactaac taaacttaga tacacctaat tttttgtagg agcatgaaac tcttaatgaa    1020
tggccaagag aagtgttgaa agcaccccca aacttgatga gaatttagag tgtatttcac    1080
ccatattgca agattgtaag tgtatttaaa tttagttaat caattaaata aatgtatttt    1140
gaattccaat aattcaagga tgaaacaaat agttcatatt gaatttaaat gttttttgaa    1200
tacttctttt tttctcaata ttgactaact agtacaacca ggtttgatta tgatttagat    1260
ttgtaccaca taagattatt aaagagaaaa acattctttg atgattcatc ttttaaattc    1320
tcaaagctcg aatacgtaaa atctaattaa tatcagcata atctcattca gaggcggagc    1380
tagccttgtg ttaggggta ttcaaacctt ctttgactga aaatttttatt atttatacat    1440
gtttaaaatt actttttaat gtatatataa tagatatcaa attctttaat ttgtatttaa    1500
ttctataaat attaaattac tttattaaaa attctaattc tgtcactcgt tcatttcatc    1560
acattcttga cggtgatggt agtgataatt acattgattg gagccacatg ggccgctact    1620
ttttaaaaag gatgaaacct tggaatgtag tgaatgttga gtctcaatag ctcaatcacg    1680
gactcaacag caaaggtaag tgccaaaaat ctgtcctctt tttcccttct ccaattggag    1740
atactgtcac cttggacaaa taatatttga aaattttggc ctaaaagtta ggtttggagc    1800
cgtatggtaa tttgataaca caaattatta tataattgat atatcaagta tatatatcca    1860
aagttgtcgc attcttcgtt tcaatttgtt tctctcacta aaattttcaa ttcacttttt    1920
aaaaaatcga taaattttta atataacttt acataacata ttcaaaatta caaaaataaa    1980
ggatattttt atatgtttat ttttaatgta agattaaata tttagaattc ttttttaagaa   2040
cggtacaagc aaattaaaag agagaaggta tattagtggg cctatgtatc tttgtataca    2100
tatgcctctc aaagagctac ctgatgagtc tatatatctt tgttgatagt gatttaacaa    2160
tttatgtatg tacgtactaa gacatgttaa ataagtacct agagaaagat ttttggaaaa    2220
gtgaaaacag caataaagaa aagtcattta aacactttcc aacaaacatt tggtaatcga    2280
ttttaattac ccacttaaac aaaactattt gtacgtaaaa tgtttaagta gaaaagagat    2340
```

-continued

```
ttttttttaa aaaaaaaga aggcaagagg tcatatatct gacccttcct taaatccccg    2400
cgtataacac tttcttttt tttgtgtgtg tatgttcagg aacatttata ttttctattt    2460
gaaatttctc attaagtcaa attcgaaatc ttttaaataa tgtagaaaaa tctcattata    2520
tttaacaatc ccacttgatg aattcctaaa cattttctat aaaataacac taaatcttta    2580
attatacata ttacatacct aactcaagca tcttgtcggt aaaaatcatt agaaaagaat    2640
tggaaatagg gaaattcata gacatatttt ggttagtatc tttgtctata agaatgggtg    2700
tgttaaagag ctagtgccat agtgtaccat tctattggta gcatttggca agagttattc    2760
cctctctcca taccaatgga gaagtttaat cttgctagag tcttattgtt gcttcttcaa    2820
cttggaactt tgttcattgc ccatgcatgt ccttattgca tgtccttatt gtccatatcc    2880
tccttccacc ccaaaacacc caaaattgcc tcctaaggtg aaaccaccct ctacacaacc    2940
tccacatgtg aaaccacctt ctaccctaa acacctaaa gatcctccaa tgtgaagcca    3000
ccttctaccc ctaaacaacc accatatgtg aaaccaccta ctaccctaa acaccctcca    3060 catgttaaac caccttccac ccctaaacac cctaaacacc cccacaaaa accatgccct    3120 cctccatctc atcatggtcc taagccacca attgtaaaac ctccacatgt accaagacct    3180
cctatagtgc atcctcctcc cattgtctct ccaccttcca cacctaaacc accaaaaaca    3240
ccaccattca ctccaaaacc accatcacca ataccaccta ttgtttcacc ccctattgtt    3300
tatccaccaa tcactccaac accacctatt gtccatccac cagtcactcc aaaaccacca    3360
tcaccaacac ctcctattgt ttcaccccc attgtttatc caccaatcac tccaacacca    3420
cctgttgtgt cacctccaat cattccaaca ccacctattg tctctccacc ttttgtcccc    3480
aatcctcccg tggtaatacc accaccctac gtgccaagtc ctccggttgt tactccaccc    3540
atagttccaa caccccctac accatgccca ccaccaccac caccagc aataatacca     3600 tcaccaccag cacaaccaac ttgccccatt gatgctctca agctaggtgc ttgtgtggac    3660
gtgttaggag gactaatcca cattggaatc ggtggaagtg ctaagcaaac atgttgtcca    3720
cttctaggag gactagtaga cttggatgca gccatttgtc tttgcacaac tattagactc    3780
aagctcttaa acataaacat cattcttccc attgctctac aggttcttat tgatgattgt    3840
ggcaagtatc cacccaaaga cttcaagtgt ccttcaacct aaatcaaggt ttccactttt    3900
tctcactttc aattattact cactcctact caatttatgt ggtacagttg acatttcaag    3960
tattaggccc aattttctta gctcggaatt tttttaaatc tctttaaata ttttgattta    4020
tactacttat tacgtagttt tcataagtat aaatttcatt tcatatatga attcacggtc    4080
aaaaatttaa agtttatttta accaatgcca cataacttag aacatacaaa tatctttttg    4140
atcaagattt ggcaattcgt atacaataat ctttagcaag taatatgtat accaacatta    4200
tgtaatatga tgcagcatat taaacaggac atttgactga tactgccgca ttgtcatagt    4260
tgaaggcaca ataaatgtgt gaaagttcaa tttccatttt atcatggcaa taaattgaga    4320
aaacaaagga gggatattaa ttaagcttta atttggcgtg tttaattagc ttttgattaa    4380
tgtactgaat gttgtatttta cattattgtt ttagggaaat actaatggta tttagtatag    4440
tggagtatga atgctgattt gattgtatga acacgaatga atgaggaaag aatcacctaa    4500
tttatcacgt gttaatct                                                 4518
```

<210> SEQ ID NO 3
<211> LENGTH: 2546
<212> TYPE: DNA

<213> ORGANISM: TPRP-F1 SHORTER PROMOTOR
<220> FEATURE:
<221> NAME/KEY: unsure
<222> LOCATION: (3)
<223> OTHER INFORMATION: "n" is any nucleic residue

<400> SEQUENCE: 3

| | | | | | |
|---|---|---|---|---|---|
| stnctagaat | aaattaactt | gattttgagt | ccatgtattt | agagatacat | gtatctggac | 60 |
| atatcaaagt | ctgataaaat | tcataatatt | aaaacataga | gtgtctttaa | gtaattagct | 120 |
| catacactag | aatgattttt | gtaagttaca | cttaaataaa | ttgttttggc | ccatgagcca | 180 |
| actgacccca | atcaagcctc | aagggcttat | atgaatcgag | tttataagcc | ctagtttcaa | 240 |
| atgagcttga | aaaattctat | ctcaactata | tccaaataat | agattggatt | ggatcgaatc | 300 |
| ccatgggcta | cgcattttga | tagctctagt | tgtaacccta | actaatgatg | aaaatatttt | 360 |
| tgacatgata | tttatttttat | taccacaatt | attttaatat | ttattttata | cataatatat | 420 |
| ttcttataaa | attactacac | ataattgtct | gatgactgta | gaagagtagt | tgacaaaata | 480 |
| ttatcgcaat | gtcattgtta | ttataggtac | aaattattaa | gtgaaagtag | aatataacgt | 540 |
| gaaatcgaat | taaaaaaata | atcagattgt | aatgaaatat | tattagagag | aagtattaaa | 600 |
| gtacctataa | acttggcaca | aattattagt | tttatttctg | tactattgac | aaccttaaaa | 660 |
| actacttgac | taactaaact | tagatacacc | taattttttg | taggagcatg | aaactcttaa | 720 |
| tgaatggcca | agagaagtgt | tgaaagcacc | cccaaacttg | atgagaattt | agagtgtatt | 780 |
| tcacccatat | tgcaagattg | taagtgtatt | taaatttagt | taatcaatta | aataaatgta | 840 |
| ttttgaattc | caataattca | aggatgaaac | aaatagttca | tattgaattt | aaatgttttt | 900 |
| tgaatacttc | ttttttttctc | aatattgact | aactagtaca | accaggtttg | attatgattt | 960 |
| agatttgtac | cacataagat | tattaaagag | aaaaacattc | tttgatgatt | catcttttaa | 1020 |
| attctcaaag | ctcgaatacg | taaaatctaa | ttaatatcag | cataatctca | ttcagaggcg | 1080 |
| gagctagcct | tgtgttaggg | ggtattcaaa | ccttctttga | ctgaaaattt | tattatttat | 1140 |
| acatgtttaa | aattactttt | taatgtatat | ataatagata | tcaaattctt | taatttgtat | 1200 |
| ttaattctat | aaatattaaa | ttactttatt | aaaaattcta | attctgtcac | tcgttcattt | 1260 |
| catcacattc | ttgacggtga | tggtagtgat | aattacattg | attggagcca | catgggccgc | 1320 |
| tactttttaa | aaaggatgaa | accttggaat | gtagtgaatg | ttgagtctca | atagctcaat | 1380 |
| cacggactca | acagcaaagg | taagtgccaa | aaatctgtcc | tcttttttccc | ttctccaatt | 1440 |
| ggagatactg | tcaccttgga | caaataatat | ttgaaaattt | tggcctaaaa | gttaggtttg | 1500 |
| gagccgtatg | gtaatttgat | aacacaaatt | attatataat | tgatatatca | agtatatata | 1560 |
| tccaaagttg | tcgcattctt | cgtttcaatt | tgtttctctc | actaaaattt | tcaattcact | 1620 |
| ttttaaaaaa | tcgataaatt | tttaatataa | ctttacataa | catattcaaa | attacaaaaa | 1680 |
| taaaggatat | ttttatatgt | ttattttttaa | tgtaagatta | aatatttaga | attcttttta | 1740 |
| agaacggtac | aagcaaatta | aaagagagaa | ggtatattag | tgggcctatg | tatctttgta | 1800 |
| tacatatgcc | tctcaaagag | ctacctgatg | agtctatata | tctttgttga | tagtgattta | 1860 |
| acaatttatg | tatgtacgta | ctaagacatg | ttaaataagt | acctagagaa | agattttttgg | 1920 |
| aaaagtgaaa | acagcaataa | agaaaagtca | tttaaacact | ttccaacaaa | catttggtaa | 1980 |
| tcgatttttaa | ttacccactt | aaacaaaact | atttgtacgt | aaaatgttta | agtagaaaag | 2040 |
| agattttttt | ttaaaaaaaa | aagaaggcaa | gaggtcatat | atctgaccct | tccttaaatc | 2100 |
| cccgcgtata | acactttctt | ttttttttgtg | tgtgtatgtt | caggaacatt | tatattttct | 2160 |

```
atttgaaatt tctcattaag tcaaattcga atcttttaa ataatgtaga aaaatctcat    2220
tatatttaac aatcccactt gatgaattcc taaacatttt ctataaaata acactaaatc    2280
tttaattata catattacat acctaactca agcatcttgt cggtaaaaat cattagaaaa    2340
gaattggaaa tagggaaatt catagacata ttttggttag tatctttgtc tataagaatg    2400
ggtgtgttaa agagctagtg ccatagtgta ccattctatt ggtagcattt ggcaagagtt    2460
attccctctc tccataccaa tggagaagtt taatcttgct agagtcttat tgttgcttct    2520
tcaacttgga actttgttca ttgccc                                        2546

<210> SEQ ID NO 4
<211> LENGTH: 1704
<212> TYPE: DNA
<213> ORGANISM: TPRP-F1 ALTERNATE PROMOTOR
<220> FEATURE:
<221> NAME/KEY: unsure
<222> LOCATION: (3)
<223> OTHER INFORMATION: "n" is any nucleic residue

<400> SEQUENCE: 4
stnaattcca ataattcaag gatgaaacaa atagttcata ttgaatttaa atgttttttg      60
aatacttctt ttttttctcaa tattgactaa ctagtacaac caggtttgat tatgatttag    120
atttgtacca cataagatta ttaaagagaa aaacattctt tgatgattca tcttttaaat     180
tctcaaagct cgaatacgta aaatctaatt aatatcagca taatctcatt cagaggcgga     240
gctagccttg tgttaggggg tattcaaacc ttctttgact gaaaatttta ttatttatac     300
atgtttaaaa ttacttttta atgtatatat aatagatatc aaattcttta atttgtattt     360
aattctataa atattaaatt actttattaa aaattctaat tctgtcactc gttcatttca     420
tcacattctt gacggtgatg gtagtgataa ttacattgat tggagccaca tgggccgcta     480 cttttttaaaa aggatgaaac cttggaatgt agtgaatgtt gagtctcaat agctcaatca    540
cggactcaac agcaaaggta agtgccaaaa atctgtcctc tttttccctt ctccaattgg     600
agatactgtc accttggaca ataatatttt gaaaattttg gcctaaaagt taggtttgga    660
gccgtatggt aatttgataa cacaaattat tatataattg atatatcaag tatatatatc    720
caaagttgtc gcattcttcg tttcaatttg tttctctcac taaaattttc aattcacttt    780
ttaaaaaatc gataaatttt taatataact ttacataaca tattcaaaat tacaaaaata    840
aaggatattt ttatatgttt attttttaatg taagattaaa tatttagaat tcttttttaag    900 aacggtacaa gcaaattaaa agagagaagg tatattagtg ggcctatgta tctttgtata    960
catatgcctc tcaaagagct acctgatgag tctatatatc tttgttgata gtgatttaac    1020
aatttatgta tgtacgtact aagacatgtt aaataagtac ctagagaaag attttttggaa   1080 aagtgaaaac agcaataaag aaaagtcatt taaacacttt ccaacaaaca tttggtaatc    1140
gattttaatt acccacttaa acaaaactat ttgtacgtaa aatgtttaag tagaaaagag    1200 atttttttt aaaaaaaaa gaaggcaaga ggtcatatat ctgaccccttc cttaaatccc    1260 cgcgtataac actttctttt tttttgtgtg tgtatgttca ggaacattta tatttctat     1320 ttgaaatttc tcattaagtc aaattcgaaa tcttttaaat aatgtagaaa atctcatta     1380 tatttaacaa tcccacttga tgaattccta aacattttct ataaaataac actaaatctt   1440
taattataca tattacatac ctaactcaag catcttgtcg gtaaaaatca ttagaaaaga    1500
attggaaata gggaaattca tagacatatt ttggttagta tctttgtcta taagaatggg    1560
```

-continued

| | |
|---|---|
| tgtgttaaag agctagtgcc atagtgtacc attctattgg tagcatttgg caagagttat | 1620 |
| tccctctctc cataccaatg gagaagttta atcttgctag agtcttattg ttgcttcttc | 1680 |
| aacttggaac tttgttcatt gccc | 1704 |

<210> SEQ ID NO 5
<211> LENGTH: 2293
<212> TYPE: DNA
<213> ORGANISM: ROLB GENE

<400> SEQUENCE: 5

| | |
|---|---|
| atgcatccca aataggcgag tgagatggaa gggaggcaat gacacgaaat ttgtctatgt | 60 |
| gtcctagata tgtaagaatt cactgatata ttgagtgtat ctagaataaa ttaacttgat | 120 |
| tttgagtcca tgtatttaga gatacatgta tctggacata tcaaagtctg ataaaattca | 180 |
| taatattaaa acatagagtg tctttaagta attagctcat acactagaat gatttttgta | 240 |
| agttacactt aaataaattg ttttggccca tgagccaact gaccccaatc aagcctcaag | 300 |
| ggcttatatg aatcgagttt ataagcccta gtttcaaatg agcttgaaaa attctatctc | 360 |
| aactatatcc aaataataga ttggattgga tcgaatccca tgggctacgc attttgatag | 420 |
| ctctagttgt aaccctaact aatgatgaaa atatttttga catgatattt atttttattac | 480 |
| cacaattatt ttaatattta ttttatacat aatatatttc ttataaaatt actacacata | 540 |
| attgtctgat gactgtagaa gagtagttga caaaatatta tcgcaatgtc attgttatta | 600 |
| taggtacaaa ttattaagtg aaagtagaat ataacgtgaa atcgaattaa aaaaataatc | 660 |
| agattgtaat gaaatattat tagagagaag tattaaagta cctataaact tggcacaaat | 720 |
| tattagtttt atttctgtac tattgacaac cttaaaaact acttgactaa ctaaacttag | 780 |
| atacacctaa ttttttgtag gagcatgaaa ctcttaatga atggccaaga gaagtgttga | 840 |
| aagcaccccc aaacttgatg agaatttaga gtgtatttca cccatattgc aagattgtaa | 900 |
| gtgtatttaa atttagttaa tcaattaaat aaatgtattt tgaattccaa taattcaagg | 960 |
| atgaaacaaa tagttcatat tgaatttaaa tgttttttga atacttcttt ttttctcaat | 1020 |
| attgactaac tagtacaacc aggtttgatt atgatttaga tttgtaccac ataagattat | 1080 |
| taaagagaaa acattctttt gatgattcat ctttttaaatt ctcaaagctc gaatacgtaa | 1140 |
| aatctaatta atatcagcat aatctcattc agaggcggag ctagccttgt gttagggggt | 1200 |
| attcaaacct tctttgactg aaaatttttat tatttataca tgtttaaaat tactttttaa | 1260 |
| tgtatatata atagatatca aattctttaa tttgtattta attctataaa tattaaatta | 1320 |
| ctttattaaa aattctaatt ctgtcactcg ttcatttcat cacattcttg acggtgatgg | 1380 |
| tagtgataat tacattgatt ggagccacat gggccgctac tttttaaaaa ggatgaaacc | 1440 |
| ttggaatgta gtgaatgttg agtctcaata gctcaatcac ggactcaaca gcaaaggtaa | 1500 |
| gtgccaaaaa tctgtcctct ttttcccttc tccaattgga gatactgtca ccttggacaa | 1560 |
| ataatatttg aaaattttgg cctaaaagtt aggtttggag ccgtatggta atttgataac | 1620 |
| acaaattatt atataattga tatatcaagt atatatatcc aaagttgtcg cattcttcgt | 1680 |
| ttcaatttgt ttctctcact aaaatttttca attcactttt taaaaaatcg atttttaatta | 1740 |
| cccacttaaa caaaactatt tgtacgtaaa atgtttaagt agaaaagaga tttttttta | 1800 |
| aaaaaaaaag aaggcaagag gtcatatatc tgacccttcc ttaaatcccc gcgtataaca | 1860 |
| cttttctttt ttttgtgtgt gtatgttcag gaacatttat attttctatt tgaaatttct | 1920 |
| cattaagtca aattcgaaat cttttaaata atgtagaaaa atctcattat atttaacaat | 1980 |

```
cccacttgat gaattcctaa acattttcta taaaataaca ctaaatcttt aattatacat    2040
attacatacc taactcaagc atcttgtcgg taaaaatcat tagaaaagaa ttggaaatag    2100
ggaaattcat agacatattt tggttagtat ctttgtctat aagaatgggt gtgttaaaga    2160
gctagtgcca tagtgtacca ttctattggt agcatttggc aagagttatt ccctctctcc    2220
ataccaatgg agaagtttaa tcttgctaga gtcttattgt tgcttcttca acttggaact    2280
ttgttcattg ccc                                                       2293

<210> SEQ ID NO 6
<211> LENGTH: 27
<212> TYPE: DNA
<213> ORGANISM: Chimeric gene TPRP-F1

<400> SEQUENCE: 6
tggtaccggg caatgaacaa agttcca                                          27
```